US008933010B2

(12) United States Patent
Scheuing et al.

(10) Patent No.: US 8,933,010 B2

(45) Date of Patent: *Jan. 13, 2015

(54) CATIONIC MICELLES WITH ANIONIC POLYMERIC COUNTERIONS COMPOSITIONS THEREOF

(71) Applicant: The Clorox Company, Oakland, CA (US)

(72) Inventors: David R. Scheuing, Pleasanton, CA (US); Travers Anderson, Pleasanton, CA (US); William L. Smith, Pleasanton, CA (US); Erika Szekeres, Pleasanton, CA (US); Rui Zhang, Kaohsiung (TW)

(73) Assignee: The Clorox Company, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/244,582

(22) Filed: Apr. 3, 2014

(65) Prior Publication Data

US 2014/0296126 A1 Oct. 2, 2014

Related U.S. Application Data

(63) Continuation of application No. 13/663,792, filed on Oct. 30, 2012, now Pat. No. 8,728,454.

(51) Int. Cl.
*C11D 3/48* (2006.01)
*A01N 25/02* (2006.01)

(52) U.S. Cl.
CPC . *C11D 3/48* (2013.01); *A01N 25/02* (2013.01)
USPC .......................................... 510/391; 510/382

(58) Field of Classification Search
None
See application file for complete search history.

(56) References Cited

U.S. PATENT DOCUMENTS

| | | | | |
|---|---|---|---|---|
| 3,620,773 | A | 11/1971 | Gabriel | |
| 4,282,109 | A | 8/1981 | Citrone et al. | |
| 4,353,806 | A | 10/1982 | Baker et al. | |
| 4,764,365 | A | 8/1988 | Boothe et al. | |
| 4,772,462 | A | 9/1988 | Boothe et al. | |
| 4,898,725 | A | 2/1990 | Giede et al. | |
| 4,940,576 | A | 7/1990 | Walsh | |
| 5,110,964 | A | 5/1992 | Hiroi et al. | |
| 5,158,766 | A | 10/1992 | Greenwald et al. | |
| 5,360,571 | A | 11/1994 | Kilgour et al. | |
| 5,444,094 | A | 8/1995 | Malik et al. | |
| 5,591,708 | A | 1/1997 | Richter | |
| 5,631,218 | A | 5/1997 | Allan et al. | |
| 5,658,915 | A | 8/1997 | Abe et al. | |
| 5,686,015 | A | 11/1997 | Willey et al. | |
| 5,888,957 | A | 3/1999 | Durbut | |
| 5,916,859 | A * | 6/1999 | Choy et al. | 510/195 |
| 6,080,387 | A | 6/2000 | Zhou et al. | |
| 6,107,266 | A | 8/2000 | Borchers et al. | |
| 6,184,188 | B1 | 2/2001 | Severns et al. | |
| 6,218,346 | B1 | 4/2001 | Sajic et al. | |
| 6,242,526 | B1 | 6/2001 | Siddiqui et al. | |
| 6,251,849 | B1 | 6/2001 | Jeschke et al. | |
| 6,270,754 | B1 | 8/2001 | Zhou et al. | |
| 6,358,909 | B1 | 3/2002 | Ochomogo et al. | |
| 6,482,392 | B1 | 11/2002 | Zhou et al. | |
| 6,524,485 | B1 | 2/2003 | Dubin et al. | |
| 6,569,952 | B1 | 5/2003 | Chen et al. | |
| 6,716,805 | B1 | 4/2004 | Sherry et al. | |
| 6,780,379 | B1 | 8/2004 | Chen et al. | |
| 6,913,686 | B2 | 7/2005 | Hilgarth | |
| 7,041,630 | B1 | 5/2006 | Barnabas et al. | |
| 7,074,459 | B2 | 7/2006 | Stockel | |
| 7,229,837 | B2 | 6/2007 | Chen | |
| 7,288,514 | B2 | 10/2007 | Knock et al. | |
| 7,334,538 | B1 | 2/2008 | Kuhns | |
| 7,381,417 | B2 | 6/2008 | Gamez-Garcia | |
| 7,470,290 | B2 | 12/2008 | Budd et al. | |
| 7,517,568 | B2 | 4/2009 | Bitowft et al. | |
| 7,569,533 | B2 | 8/2009 | Lin et al. | |
| 7,579,400 | B2 | 8/2009 | Bavouzet et al. | |
| 7,608,573 | B1 | 10/2009 | Falk et al. | |
| 7,618,931 | B1 | 11/2009 | Scheuing et al. | |
| 7,629,305 | B1 | 12/2009 | Lestage et al. | |
| 7,700,540 | B2 | 4/2010 | Deleo et al. | |
| 7,871,972 | B2 | 1/2011 | Sengupta | |

(Continued)

FOREIGN PATENT DOCUMENTS

| | | | |
|---|---|---|---|
| EP | 0335404 | A2 | 10/1990 |
| EP | 423014 | A2 | 4/1991 |
| EP | 0195895 | B1 | 8/1992 |
| EP | 0472107 | B1 | 12/1994 |
| EP | 0422508 | B2 | 3/1998 |

(Continued)

OTHER PUBLICATIONS

Jan. 11, 2013; PCT International Search Report PCT/US 12/63433; The Clorox Company.

(Continued)

*Primary Examiner* — Brian Gulledge
*Assistant Examiner* — Celeste A Roney
(74) *Attorney, Agent, or Firm* — Alok Goel

(57) ABSTRACT

The invention relates to polymer-micelle complex. The polymer-micelle complexes include a positively charged micelle selected from the group consisting of a monomeric quaternary ammonium compound, a monomeric biguanide compound, and mixtures thereof. The positively charged micelle is electrostatically bound to a water-soluble polymer bearing a negative charge. The polymer does not comprise block copolymer, latex particles, polymer nanoparticles, cross-linked polymers, silicone copolymer, fluorosurfactant, or amphoteric copolymer. The compositions do not form a coacervate, and do not form a film when applied to a surface.

13 Claims, No Drawings

(56) References Cited

U.S. PATENT DOCUMENTS

| | | | | |
|---|---|---|---|---|
| 7,888,306 | B2 | 2/2011 | Hughes et al. | |
| 7,939,486 | B2 | 5/2011 | Falk et al. | |
| 7,939,487 | B2 | 5/2011 | Scheuing et al. | |
| 7,939,488 | B2 | 5/2011 | Scheuing et al. | |
| 8,058,837 | B2 | 11/2011 | Beers et al. | |
| 8,728,454 | B1 * | 5/2014 | Scheuing et al. | 424/78.27 |
| 2001/0044401 | A1 | 11/2001 | Perkins et al. | |
| 2003/0073606 | A1 | 4/2003 | Howell et al. | |
| 2003/0114342 | A1 | 6/2003 | Hall | |
| 2003/0186830 | A1 | 10/2003 | Godfroid et al. | |
| 2004/0013638 | A1 | 1/2004 | Aubay et al. | |
| 2004/0052748 | A1 | 3/2004 | Vondruska | |
| 2004/0082925 | A1 | 4/2004 | Patel | |
| 2005/0048005 | A1 | 3/2005 | Stockel | |
| 2005/0054546 | A1 | 3/2005 | Glick et al. | |
| 2005/0119221 | A1 | 6/2005 | Xia et al. | |
| 2005/0276778 | A1 | 12/2005 | Chen et al. | |
| 2006/0211593 | A1 | 9/2006 | Hand et al. | |
| 2006/0275337 | A1 | 12/2006 | Cohen Stuart et al. | |
| 2006/0293197 | A1 | 12/2006 | Hatano et al. | |
| 2006/0293213 | A1 | 12/2006 | Uehara et al. | |
| 2007/0041932 | A1 | 2/2007 | Jeong | |
| 2007/0196284 | A1 | 8/2007 | Tournier et al. | |
| 2008/0242582 | A1 | 10/2008 | Sengupta et al. | |
| 2009/0036404 | A1 | 2/2009 | MacLeod | |
| 2009/0048143 | A1 | 2/2009 | Iverson et al. | |
| 2009/0104430 | A1 | 4/2009 | Cordial et al. | |
| 2009/0196845 | A1 | 8/2009 | Barniak et al. | |
| 2010/0160201 | A1 | 6/2010 | Scheuing et al. | |
| 2010/0234319 | A1 | 9/2010 | Yu | |
| 2010/0240566 | A1 * | 9/2010 | Meine et al. | 510/276 |
| 2010/0291169 | A1 | 11/2010 | Liesenfeld et al. | |
| 2010/0314118 | A1 | 12/2010 | Quintero | |
| 2011/0010986 | A1 | 1/2011 | Alarco | |
| 2011/0046033 | A1 | 2/2011 | Zhang | |
| 2011/0183852 | A1 | 7/2011 | Yeung | |
| 2011/0236450 | A1 * | 9/2011 | Scheuing et al. | 424/405 |
| 2011/0236582 | A1 | 9/2011 | Scheuing et al. | |

FOREIGN PATENT DOCUMENTS

| | | | |
|---|---|---|---|
| EP | 1106677 | A1 | 6/2001 |
| EP | 0904052 | B1 | 12/2002 |
| EP | 1779896 | B1 | 8/2012 |
| JP | 01132692 | A | 5/1989 |
| WO | 9517817 | A1 | 7/1995 |
| WO | 9738673 | A1 | 10/1997 |
| WO | 9745510 | A1 | 12/1997 |
| WO | 9844791 | A1 | 10/1998 |
| WO | WO 0061712 | | 10/2000 |
| WO | 0123511 | A1 | 4/2001 |
| WO | 2005030282 | A1 | 4/2005 |
| WO | 2010106700 | A1 | 9/2010 |
| WO | 2010143934 | A1 | 12/2010 |

OTHER PUBLICATIONS

Mar. 12, 2013; PCT International Search Report PCT/US2012/63436;The Clorox Company.

Kim et al., Biodegradable Photo-Crosslinked Thin Polymer Networks Based on Vegetable Oil Hydroxy Fattty Acids J Am Oil Chem Soc (2010) 87:1451?1459, entire document.

Built in Dishwashers vs. Hand Washing: Which is Greener?: retrieved from internet: http://www.treehugger.com/kitchen-design/built-in-dishwashers-vs-hand-washing-which-is-greener.html. Retrieved on Aug. 19, 2014.

Dishwasher Not Filling With Enough Water: retrieved from Internet: http://partsdr.com/blog/dishwasher-not-filling-with-enough-water/. Retrieved on Aug. 19, 2014.

Perfume: retrieved from internet: http://en.wikipedia.org/wiki/Perfume. Retrieved on Aug. 19, 2014.

Acusol 823, Rheology Modifier and Stabilizer; Rohm and Hass; p. 1-6; Jan. 2003.

* cited by examiner

CATIONIC MICELLES WITH ANIONIC POLYMERIC COUNTERIONS COMPOSITIONS THEREOF

CROSS-REFERENCE TO RELATED APPLICATIONS

The present application is a continuation of co-pending U.S. patent application Ser. No. 13/663,792, filed on Oct. 30, 2012. The present application is also related to U.S. patent application Ser. No. 13/663,830, filed on Oct. 30, 2012 and U.S. patent application Ser. No. 13/663,862, filed on Oct. 30, 2012. The disclosure of each of the above applications is incorporated by reference in its entirety.

BACKGROUND OF THE INVENTION

1. The Field of the Invention

The present invention relates to polymer-micelle complexes.

2. Description of Related Art

Cleaning product formulations, including those which contain common antimicrobial agents such as quaternary ammonium compounds and biguanides such as chlorhexidine and alexidine, rely on surfactants and mixtures of surfactants to deliver cleaning (detergency) and antimicrobial efficacy. A key aspect of these processes is the interaction of the surfactants and antimicrobial agents with the solid surfaces of the materials being cleaned, as well as the surfaces of microorganisms, together with the effects of the formulations on the air-water interface (surface tension). Reduction of the surface tension of aqueous formulations, which is directly related to the effectiveness of the wetting of solid surfaces and hence the detergency and antimicrobial processes, can be manipulated through the use of mixtures of surfactants, as is known in the art.

At a molecular level, surfactants and surfactant mixtures in aqueous media exhibit the ability to adsorb at the air-water, solid-water, and oil-water interfaces, and this adsorption is hence responsible for a wide range of phenomena, including the solubilization of oils in the detergency process, the changes in the properties of solids and dispersions of solids, and the lowering of the surface tension of water. Adsorption of surfactants at interfaces is generally known to increase with surfactant concentration up to a total surfactant concentration known as the critical micelle concentration (CMC). At the CMC, surfactants begin to form aggregates in the bulk solution known as micelles, in equilibrium with the monomeric species of surfactants which adsorb onto the interfaces.

The details of the structures and sizes of the micelles, as well as the properties of the adsorbed layers of surfactants or surfactant mixtures, depend on the details of the molecular shape and charges, if any, on the hydrophilic "headgroups" of the surfactants. Strongly charged headgroups of surfactants tend to repel each other at interfaces, opposing the efficient packing of the surfactants at the interface, and also favoring micelle structures that are relatively small and spherical. The charged headgroups of many surfactants, such as the quaternary ammonium compounds, will also introduce a counterion of opposite charge, for example a chloride or bromide ion, into formulations.

It is known that the nature of the counterion can affect the repulsion between charged surfactants in micelles and adsorbed layers through a partial screening of the headgroup charges from one another in surfactant aggregates like micelles. It is also well known that addition of simple electrolytes, such as sodium chloride, into aqueous solutions can also be used to increase the screening of like headgroup charges from each other, and thus is a common parameter used to adjust the properties of surfactant micelles, such as size and shape, and to adjust the adsorption of surfactants onto surfaces.

Addition of significant amounts of simple electrolytes into many formulations, such as hard surface spray cleaners or nonwoven wipes loaded with a cleaning lotion, is undesirable due to residues left behind upon drying of the formulations. An alternative method to adjusting the properties of such formulations, including the wetting of solid surfaces and the antimicrobial activity, is to include significant amounts of volatile organic solvents such as lower alcohols or glycol ethers. Volatile organic solvents, however, are coming under increasing regulation due to their potential health effects, and are not preferred by the significant fraction of consumers who desire efficacious cleaning and disinfecting products with a minimum of chemical actives, including volatiles. In the healthcare industry, efficacious formulations comprising quaternary ammonium compounds and lower alcohols are known, but are viewed as having shortcomings in terms of the potential for irritation of confined patients. Such products pose similar risks to cleaning and clinical personnel who may be exposed to such products on a daily basis.

There is an increasing interest from consumers, and a known need in the healthcare and housekeeping industries, to reduce the number of microorganisms on fabrics while using familiar equipment such as washing machines. Concentrated products are required for such an application, due to the high dilution level of the product in the rinsewater, typically by a factor of about 600 times dilution. In the case of formulations comprising quaternary ammonium compounds, high concentrations of the quaternary ammonium compounds in the concentrate are needed in order to ensure an adequate amount of adsorption occurs in a kinetically relevant time onto the microbes under dilution use conditions. As detailed above, it is desirable, yet very difficult, to manipulate (i.e., reduce) the CMC of the quaternary ammonium compound in such an application. Thus very high concentrations of quaternary ammonium compounds, which tend to be hazardous to the skin and eyes, are used in the concentrates, in combination with high temperatures and long exposure times.

Thus, there is an ongoing need for methods and compositions offering fine control of the properties of surfactant aggregates comprising cationic species, especially antimicrobial species such as quaternary ammonium compounds and biguanides.

BRIEF SUMMARY OF THE INVENTION

One aspect of the invention is directed to a composition comprising a polymer-micelle complex comprising a positively charged micelle comprising a water-soluble cationic material selected from the group consisting of a monomeric quaternary ammonium compound, a monomeric biguanide compound, and mixtures thereof. The micelle is electrostatically bound to a water-soluble polymer bearing a negative charge. The water-soluble polymer bearing a negative charge comprises a hybrid copolymer derived from a synthetic monomer or monomers chain terminated with a hydroxyl-containing natural material synthesized with a free radical initiator. The polymer does not comprise block copolymer, latex particles, polymer nanoparticles, cross-linked polymers, silicone copolymer, fluorosurfactant, or amphoteric copolymer. The complex advantageously does not form a coacervate, and does not form a film on a surface (e.g., a durable film remaining after application of the composition to the surface).

Another embodiment of the invention is directed to a composition comprising a polymer-micelle complex comprising a positively charged micelle comprising a water-soluble cationic material selected from the group consisting of a monomeric quaternary ammonium compound, a monomeric biguanide compound, and mixtures thereof. The micelle is electrostatically bound to a water-soluble polymer bearing a negative charge. The water-soluble polymer bearing a negative charge comprises a hybrid copolymer derived from a synthetic monomer or monomers chain terminated with a hydroxyl-containing natural material synthesized with a free radical initiator. The polymer does not comprise block copolymer, latex particles, polymer nanoparticles, cross-linked polymers, silicone copolymer, fluorosurfactant, or amphoteric copolymer. The composition advantageously does not form a coacervate, and does not include alcohols (e.g., particularly lower alcohols) or glycol ethers.

Another embodiment of the invention is directed to a composition comprising a polymer-micelle complex comprising a positively charged micelle that is electrostatically bound to a water-soluble polymer bearing a negative charge. The water-soluble polymer does not comprise block copolymer, latex particles, polymer nanoparticles, cross-linked polymers, silicone copolymer, fluorosurfactant, or amphoteric copolymer. The composition advantageously does not form a coacervate and does not form a film on a surface. In addition to the polymer-micelle complex, the composition further comprises an oxidant.

Further features and advantages of the present invention will become apparent to those of ordinary skill in the art in view of the detailed description of preferred embodiments below.

DETAILED DESCRIPTION OF THE PREFERRED EMBODIMENTS

I. Definitions

Before describing the present invention in detail, it is to be understood that this invention is not limited to particularly exemplified systems or process parameters that may, of course, vary. It is also to be understood that the terminology used herein is for the purpose of describing particular embodiments of the invention only, and is not intended to limit the scope of the invention in any manner.

All publications, patents and patent applications cited herein, whether supra or infra, are hereby incorporated by reference in their entirety to the same extent as if each individual publication, patent or patent application was specifically and individually indicated to be incorporated by reference.

The term "comprising" which is synonymous with "including," "containing," or "characterized by," is inclusive or open-ended and does not exclude additional, unrecited elements or method steps.

The term "consisting essentially of" limits the scope of a claim to the specified materials or steps "and those that do not materially affect the basic and novel characteristic(s)" of the claimed invention.

The term "consisting of" as used herein, excludes any element, step, or ingredient not specified in the claim.

It must be noted that, as used in this specification and the appended claims, the singular forms "a," "an" and "the" include plural referents unless the content clearly dictates otherwise. Thus, for example, reference to a "surfactant" includes one, two or more such surfactants.

The term water-soluble polymer as used herein means a polymer which gives an optically clear solution free of precipitates at a concentration of 0.001 grams per 100 grams of water, preferably 0.01 grams/100 grams of water, more preferably 0.1 grams/100 grams of water, and even more preferably 1 gram or more per 100 grams of water, at 25° C.

As used herein, the term "substrate" is intended to include any material that is used to clean an article or a surface. Examples of cleaning substrates include, but are not limited to nonwovens, sponges, films and similar materials which can be attached to a cleaning implement, such as a floor mop, handle, or a hand held cleaning tool, such as a toilet cleaning device.

As used herein, the terms "nonwoven" or "nonwoven web" means a web having a structure of individual fibers or threads which are interlaid, but not in an identifiable manner as in a knitted web.

As used herein, the term "polymer" as used in reference to a substrate (e.g., a nonwoven substrate) generally includes, but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the molecule. These configurations include, but are not limited to isotactic, syndiotactic and random symmetries.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

In the application, effective amounts are generally those amounts listed as the ranges or levels of ingredients in the descriptions, which follow hereto. Unless otherwise stated, amounts listed in percentage ("wt %'s") are in wt % (based on 100 weight % active) of the particular material present in the referenced composition, any remaining percentage being water or an aqueous carrier sufficient to account for 100% of the composition, unless otherwise noted. For very low weight percentages, the term "ppm" corresponding to parts per million on a weight/weight basis may be used, noting that 1.0 wt % corresponds to 10,000 ppm.

II. Introduction

The present inventors have now determined that the use of water-soluble polymers comprising groups which bear or are capable of bearing an electrostatic charge as counterions (polymeric counterions) for micelles comprising at least one ionic surfactant selected such that the net electrostatic charge on the micelle is opposite to that of the polymeric counterion can yield, simultaneously, very fine control of the interactions between the headgroups of the ionic surfactant as well as the adsorption of the ionic surfactant at the air-liquid and solid-liquid interface when compositions are adjusted such that precipitates or coacervates are completely absent from at least some embodiments of the compositions.

Surprisingly, such compositions in which micelles with polymeric counterions exist as soluble, thermodynamically stable aggregates exhibit very high adsorption activity at both the air-liquid and solid-liquid interfaces. Such characteristics completely eliminate the need to adjust formulations such that they change their solubility, forming coacervates or precipitates, in order to deliver adsorption of useful amounts of ionic surfactant and polymer to these interfaces. The micelle-polymer complexes formed when a water-soluble polymer comprising groups which bear or are capable of bearing an electrostatic charge opposite to that of a micelle are usually found to be somewhat larger than the micelles alone. The addition of a water-soluble polymer bearing electrostatic charges opposite to that of at least one surfactant in aqueous solutions often can reduce the CMC of the given surfactant by a significant fraction, which can also have the effect of reducing the cost of certain formulations.

Fine control of surfactant interactions within micelles via addition of oppositely charged polymers according to the invention has also been found to increase the oil solubilization ability of the micelles to an unexpected degree. Without being bound by theory, it is believed that this effect is due to the uniquely high counter ion charge density carried by the charged polymer, which is distinctly different from regular counter ion effect provided by typical salting out electrolytes. This is thought to increase the degree of counter ion association of charged polymers compared to regular electrolytes, even at very low polymer concentrations, which in turn promotes increases in micellar size and an increase in oil solubilization efficiency. The inventors have discovered that the oil solubilization boosting effect develops only if the interactions are fine-tuned such that the system is fully free of coacervate yet is near the water soluble/coacervate phase boundary.

Formulations comprising mixed micelles of a cationic germicide (quaternary ammonium compound or a water-soluble salt of a biguanide such as chlorhexidine or alexidine), optionally a second surfactant such as an amine oxide, and a water-soluble polymer bearing an anionic charge can be made with control of the size and net electrostatic charge. It is believed, without being bound by theory, that the anionic polymers act as polymeric counterions to the cationically charged micelles, either increasing the size of these micelles or collecting groups of these micelles into soluble, thermodynamically stable aggregates which have enhanced activity at solid surface-aqueous solution interfaces, including the surfaces of microorganisms such as bacteria, viruses, fungi, and bacterial spores. This reduces or even eliminates the need for the presence of an alcohol to enhance or “potentiate” the antimicrobial performance of the cationic biocide.

In one embodiment, the compositions can comprise alcohol. In another embodiment, the compositions can be completely free of water-miscible lower alcohols. Similarly, the compositions can comprise water-miscible glycol ethers or be completely free of the materials, sometimes referred to as “co-solvents” or “co-surfactants”. Compositions free of the lower alcohols or glycol ethers not only can provide acceptable antimicrobial performance at lower cost, but also reduce irritation to patients and healthcare workers, while providing formulations which can be considered more environmentally friendly or sustainable due to lowered total actives levels and lack of volatile organic compounds. Those embodiments that are free of alcohols or cosolvents are especially suited as sanitizing cleaners, disinfecting cleaners or treatments for pets in home or veterinary applications.

Surprisingly, the compositions, even without alcohol, show inactivation of non-enveloped viruses such as rhinovirus, even though cationic biocides are typically not considered as active against such microorganisms. It is believed, without being bound by theory, that the interfacial activity of the micelles with polymeric counterions is so significant that the viral proteins are disrupted, denatured or otherwise damaged such that the viral particles are rendered non-infective, even when they are exposed to significant dilutions such as those during the microbiological test protocols. Surprisingly, the compositions, even without alcohol, exhibit activity against mycobacteria, (bacteria responsible for tuberculosis), which are heretofore known to be relatively resistant to the actions of cationic germicides in aqueous formulations lacking a co-solvent or alcohol. Such resistance is thought to be due to the thick, waxy outer membranes characteristic of this type of bacteria.

The compositions may be useful as ready to use cleaners, and may be applied via spraying or pouring, but may also be delivered by loading onto nonwoven substrates to produced pre-moistened wipes. The compositions may also be provided as concentrates that are diluted by the consumer (e.g., with tap water). Such concentrates may comprise a part of a kit for refilling a container (also optionally included within such a kit), such as an empty trigger sprayer. The compositions may also be provided as concentrates for single-use (unit dose) products for cleaning floors, windows, counters, etc. Concentrated dishwashing liquids that provide antibacterial performance upon very high dilutions may be formulated, as may concentrates which can deliver sanitization of laundry via addition to ordinary washloads. Such compositions and results may be achieved without inclusion of triclosan. Such concentrated products also can provide protection against the growth of biofilms and associated outgrowth of molds in drain lines associated with automatic dishwashers, laundry washing machines, and the like, reducing undesirable odors which are sometimes encountered by consumers.

Concentrated forms of the formulations may also be provided which may be diluted by the consumer to provide solutions that are then used. Concentrated forms suitable for dilution via automated systems, in which the concentrate is diluted with water, or in which two solutions are combined in a given ratio to provide the final use formulation are possible.

The formulations may be in the form of gels delivered to a reservoir or surface with a dispensing device. They may optionally be delivered in single-use pouches comprising a soluble film.

The superior wetting, spreading, and cleaning performance of the systems make them especially suitable for delivery from aerosol packages comprising either single or dual chambers.

The compositions are useful in providing a reversal in the native surface charge (i.e., zeta potential) of bacterial endospores and other microorganisms from anionic (negative) to cationic (positive), or at least to less anionic as a result of contact with the compositions. Such a change in charge increases the electrostatic binding of the microorganisms to cleaning implements such as pre-moistened nonwoven wipes, which typically have a native anionic (negative) charge, hence improving the removal of the microorganisms from surfaces being cleaned. Because the compositions provide robust adsorbed layers of germicidal materials such as quaternary ammonium compounds and biguanides, they are able to kill bacteria which arise from the germination of endospores under favorable environmental conditions. Such compositions may thus find utility in various applications including combating weaponized spores such as *Bacillus Anthracis*. Low residue treatment solutions for surfaces which may be infrequently cleaned and which may be subject to outgrowth of bacteria or molds from contamination by air-borne spores can be produced with the compositions. In other words, the compositions do not result in the formation of a durable film on a surface after application. Simple rinsing is sufficient to remove any residue, and even without rinsing, those embodiments of the invention that do exhibit a residue do not form macroscopic durable films. Thus, any remaining residue does not constitute a film, but is easily disturbed, destroyed, or otherwise removed.

The invention also contemplates use of the polymer-micelle complexes for delivering improved sanitization of surfaces and protection of treated surfaces through the same mechanism of enhanced adsorption of cationic biocides such as quaternary ammonium salts and biguanides onto living bacteria, bacterial endospores, fungal spores, and viruses. Examples of antimicrobial activity exhibited by the inventive compositions include, but are not limited to killing of living bacteria, killing of bacteria upon germination from bacterial endospores, killing of living fungi, killing of fungi upon germination from spores, damage to the proteins or lipids of viral capsids resulting in decreased or inhibited infectivity to a target host, adsorption onto the proteins of viral capsids resulting in blockage of the protein from a target site in a host, or increased binding of a bacterial endospore, a fungal spore, or a virus to a non-animate surface resulting in a decrease in physical transmission to a host which in turn decreases the transmission of disease of the host or addition contamination of other surfaces. Depending on application use, the surface may be hard, soft, animate (e.g., skin), non-animate, or other type surface.

III. Definition of Dnet and P/Dnet Parameters

As will be shown in the examples below, very fine control of the interactions between micelles comprising an ionic surfactant and water-soluble polymers bearing electrostatic charges opposite to that of the micelles, and hence functioning as polymeric counterions to the micelles, can be achieved through manipulation of the relative number of charges due to ionic surfactants in the system and those charges due to the water-soluble polymer.

Mixtures of surfactants, including mixtures of ionic and nonionic surfactants, may be employed. A convenient way to describe the net charge on the micelles present in the formulations of the instant invention is to calculate the total number of equivalents of the charged headgroups of the surfactants, both anionic and cationic, followed by a determination of which type of charged headgroup is in excess in the formulation.

Surfactants bearing two opposite electrostatic charges in the formulations, such as carboxy-betaines and sulfo-betaines, act as "pseudo-nonionic" surfactants in the compositions of the instant invention, since the net charge on them will be zero. Thus, the calculation of Dnet will not involve the concentration of such pseudo-nonionic surfactants. Similarly, phosphatidyl choline, an edible material which is a major component of the surfactant commonly referred to as lecithin, contains both an anionically charged phosphate group and a cationically charged choline group in its headgroup region, and thus would be treated as pseudo-nonionic in the inventive compositions. On the other hand, a material such as phosphatidic acid, which contains only an anionically charged phosphate group as its headgroup, would contribute to the calculation of Dnet, as described below.

Some surfactants, such as amine oxides, may be uncharged (nonionic) over a wide range of pH values, but may become charged (e.g. cationically in the case of amine oxides) at acidic pH values, especially below about pH 5. Although such components may not contain two permanent and opposite electrostatic charges, applicants have found that they may be treated explicitly as nonionic surfactants in the inventive formulations. As taught herein, inventive compositions which are free of coacervates and precipitates that comprise mixed micelles of an amine oxide and a cationic germicide such as a quaternary ammonium compound and a water-soluble polymer bearing anionic charges may be readily formed through adjustment of the P/Dnet parameter, the Dnet parameter, and/or the presence of adjuvants such as electrolytes, without regard to the precise value of any cationic charge present on the amine oxide.

Two parameters can be defined for any mixture of surfactants comprising headgroups bearing, or capable or bearing, anionic or cationic charges or mixtures of both, said parameters being D anionic and D cationic.

D anionic will be defined as—

$$D\ \text{anionic}=(-1)\times(Eq\ \text{anionic})$$

D cationic will be defined as—

$$D\ \text{cationic}=(+1)\times(Eq\ \text{cationic})$$

A final parameter expressing the net charge on the micelles is Dnet, which is simply the sum of the parameters D anionic and D cationic, i.e., $$D\text{net}=D\ \text{cationic}+D\ \text{anionic}$$

In the expressions above, Eq anionic is the sum of the total number of equivalents or charges due to the headgroups of all anionic surfactants present. For a formulation comprising a single surfactant with a headgroup bearing or capable of bearing an anionic charge:

$$Eq\ \text{anionic}_1=(C\ \text{anionic}_1\times Q\ \text{anionic}_1)/M\ \text{anionic}_1$$

wherein C $\text{anionic}_1$ is the concentration of a surfactant with anionic headgroups in grams/per 100 grams of the formulation or use composition, Q $\text{anionic}_1$ is a number representing the number of anionic charges present on the surfactant, which may be viewed as having the units equivalents per mole, and M $\text{anionic}_1$ is the molecular weight of the surfactant in grams/mole.

For a formulation comprising two different surfactants with anionic headgroups, the parameter Eq anionic would be calculated as the sum:

$$Eq\ \text{anionic}=Eq\ \text{anionic}_1+Eq\ anionic_2=(C\ \text{anionic}_1\times Q\ anionic_1)/M\ \text{anionic}_1+(C\ \text{anionic}_2\times Q\ anionic_2)/M\ \text{anionic}_2$$

Commercially available surfactants are often mixtures of materials due to the presence of a distribution in the number of, for example, methylene groups in the hydrophobic "tails" of the surfactant. It is also possible that a distribution in the number of charged "headgroups" per molecule could exist. In practical work with commercial materials, it may also be acceptable to use an "average" molecular weight or an "average" number of anionic (or cationic) charges per molecule quoted by the manufacturer of the surfactant. In the calculation of D anionic (or D cationic), it may also be acceptable to use values of the Eq anionic (or Eq cationic) derived from direct analysis of a surfactant raw material.

In the expressions above, Eq cationic is the sum of the total number of equivalents or charges due to the headgroups of all cationic surfactants present. For a formulation comprising a single surfactant with a headgroup bearing or capable of bearing a cationic charge:

$$Eq\ \text{cationic}_1=(C\ \text{cationic}_1\times Q\ cationic_1)/M\ \text{cationic}_1$$

wherein C $\text{cationic}_1$ is the concentration of a surfactant with cationic headgroups in grams/per 100 grams of the formulation or use composition, Q $\text{cationic}_1$ is a number representing the number of cationic charges present on the surfactant, which may be viewed as having the units equivalents per mole, and M $cationic_1$ is the molecular weight of the surfactant in grams/mole. In cases where the formulation comprises more than one surfactant with cationic headgroups, the summation of the equivalents of cationic headgroups would be performed as in the case of the anionic surfactants described above.

As an example, consider a formulation comprising a mixture of a single anionic surfactant and a single nonionic surfactant, but lacking a cationic surfactant. Furthermore, consider the anionic surfactant is present at a concentration of 2 wt % or 2 grams/100 grams of the formulation, has one group capable of developing an anionic charge per molecule, and has a molecular weight of 200 grams/mole.

Then Eq anionic=(2×1)/200=0.01 equivalents/100 g in the formulation.

Then, D anionic=(−1)×(0.01)=−0.01.

And D cationic=0.

Thus, Dnet=(0−0.01)=−0.01.

As a second example, consider a formulation comprising a mixture of a single anionic surfactant, a single nonionic surfactant, and a single cationic surfactant which is a germicidal quaternary ammonium compound. Furthermore, consider the anionic surfactant is present at a concentration of 2 wt % or 2 grams/100 grams of the formulation, has one group capable of developing an anionic charge per molecule, and has a molecular weight of 200 grams/mole. Furthermore, consider the cationic surfactant is present in the formulation at a concentration 0.1 wt %/Q or 0.1 grams/100 grams of the formulation, has one group capable of developing a cationic charge per molecule, and has a molecular weight of 300 grams/mole.

Then Eq anionic=(2×1)/200=0.01 equivalents/100 g in the formulation.

And Eq cationic=−(0.1×1)/300=0.00033 equivalents/100 g in the formulation.

Then, D anionic=(−1)×(0.01)=−0.01.

And D cationic=(1)×(0.00033)=+0.00033.

Thus, Dnet=+0.00033+(−0.01)=−0.00967.

This negative value clearly indicates that the number of anionically charged headgroups in the mixed micelles comprising the anionic, nonionic, and cationic surfactants present in the formulation exceed that of the cationically charged headgroups.

A second parameter which can be used to describe the instant invention and the interactions between a polymeric counterion and surfactant micelles bearing a net charge is the ratio P/Dnet. P is the number of charges (in equivalents) due to the polymeric counterion present per 100 grams of the formulation and can be calculated as follows:

P=(C polymer×F polymer×Q polymer×Z)/M polymer, where C polymer is the concentration of the polymer in the formulation in grams/100 grams of formulation, F polymer is the weight fraction of the monomer unit bearing or capable of bearing a charge with respect to the total polymer weight and thus ranges from 0 to 1. Q polymer is the number of charges capable of being developed by the monomer unit capable of bearing a charge and can be viewed as having the units equivalents per mole, Z is an integer indicating the type of charge developed by the monomer unit, and is equal to +1 when the monomer unit can develop a cationic charge or is equal to −1 when the monomer unit can develop an anionic charge, and M polymer is the molecular weight of the monomer unit capable of developing a charge, in grams/mole.

For example, consider a formulation comprising polyacrylic acid homopolymer (PAA) as a water-soluble polymeric counterion. PAA is capable of developing 1 anionic charge per acrylic acid monomer unit (which has a molecular weight of 72 grams/mole), and hence Q polymer=1 and Z=−1. In addition, the polymer is a homopolymer, so F polymer=1. If the PAA is present in the formulation at a concentration of 0.1 grams/100 grams of the formulation, the value of P would be calculated as follows:

$$P=(0.1\times1\times1\times-1)/72=-0.00139.$$

Using the Dnet value of −0.00967 calculated in the example described above for a mixture of an anionic, cationic, and nonionic surfactant, the ratio P/Dnet would be calculated as:

$$P/D\text{net}=(-0.00139)/(-0.00967)=+0.144$$

This positive value of P/Dnet not only indicates the ratio of the charges due to the polymeric counterion and the net charge on the mixed micelles, but also indicates, since it is a positive number, that the charge on the polymeric counterion and the net charge on the mixed micelles are the same, both being anionic. In this case, there would be no net electrostatic interaction between the polymeric counterion and the mixed micelles expected, and hence the example would not be within the scope of the instant invention, which requires that the polymeric counterion must be of opposite charge to that of the headgroups of the surfactant or mixture of surfactants comprising the micelle.

Now consider another example in which the formulation comprises a mixture of a single anionic surfactant, a single nonionic surfactant, and a single cationic surfactant and a single cationic surfactant which is a germicidal quaternary ammonium compound. Furthermore, consider the anionic surfactant is present at a concentration of 0.2 wt % or 0.2 grams/100 grams of the formulation, has one group capable of developing an anionic charge per molecule, and has a molecular weight of 200 grams/mole. Furthermore, consider the cationic surfactant is present in the formulation at a concentration 1.0 wt % or 1.0 grams/100 grams of the formulation, has one group capable of developing a cationic charge per molecule, and has a molecular weight of 300 grams/mole.

Then Eq anionic=(0.2×1)/200=0.001 equivalents/100 g in the formulation.

And Eq cationic=(1.0×1)/300=0.00333 equivalents/100 g in the formulation.

Then, D anionic=(−1)×(0.001)=−0.001.

And D cationic=(1)×(0.00333)=+0.00333.

Thus, Dnet=+0.00333+(−0.001)=+0.00233. This positive value clearly indicates that the number of cationically charged headgroups in the mixed micelles comprising the anionic, nonionic, and cationic surfactants present in the formulation exceed that of the anionically charged headgroups. Such mixed micelles would be suitable for interaction with a polymeric counterion bearing anionic charges.

Continuing this example, now consider that the formulation also comprises a polyacrylic acid homopolymer (PAA) as a water-soluble polymeric counterion. PAA is capable of developing 1 anionic charge per acrylic acid monomer unit (which has a molecular weight of 72 grams/mole), and hence Q polymer=1 and Z=−1. In addition, the polymer is a homopolymer, so F polymer=1. If the PAA is present in the formulation at a concentration of 0.1 grams/100 grams of the formulation, the value of P would be calculated as follows:

$$P=(0.1\times1\times1\times-1)/72=-0.00139.$$

Thus, for this formulation, P/Dnet would be calculated as:

$$P/D\text{net}=(-0.00139)/(+0.00233)=-0.5966.$$

This negative value of P/Dnet indicates that the charges on the polymeric counterion (PAA) and the mixed micelles are opposite to one another, indicating that there may be an electrostatic interaction between the PAA and the micelles, and hence the composition may be within the scope of the instant invention. Of course, the value of P/Dnet also indicates the ratio of the charges due to the polymeric counterion and the net charge on the mixed micelles.

Alternatively, if the number of equivalents of charged groups present per gram of polymer is available from the manufacturer, or can be derived from the synthetic route used to create the polymer, or can be derived from analysis of the polymer, then P may also be calculated based on that information.

For example, P=(C polymer×Eq polymer×Z), where C polymer and Z are defined as above, and Eq polymer is the number of equivalents of groups per gram of polymer with a charge consistent with the value of Z used. For example, if a water-soluble polymer that is described as having 0.0139 equivalents per gram of polymer (actives) of an anionically charged monomer, and this polymer is used in a formulation at a concentration of 0.1 grams/100 grams of the formulation, P is calculated as follows:

$$P=(0.1\times0.0139\times-1)=-0.00139.$$

This value of P, with the same Dnet value used in the example above in which the micelles comprising an anionic surfactant, a nonionic surfactant and a cationic surfactant which is a quaternary ammonium compound, may then be used to calculate the ratio P/Dnet.

$$P/D\text{net}=(-0.00139)/(-0.00233)=-0.5966,$$

which yields the same result as described above.

In the case of copolymers comprising more than one monomer of like charge or capable of developing a like charge, then the P value calculated for the formulation would be the sum of the P values calculated for each of the appropriate monomers comprising the polymer used.

Finally, in practical work, the absolute value of P/Dnet is an indicator of which charges are in excess and which are in deficiency in formulations of the instant invention. When the absolute value of P/Dnet is greater than 0 but less than 1, the number of charges due to groups on the polymeric counterion is less than the net number of charges due to the headgroups of the ionic surfactant or surfactants comprising the micelles, i.e. the polymeric counterion is in deficiency. When the absolute value of P/Dnet is greater than 1, the polymeric counterion is in excess, and of course, when the absolute value of P/Dnet=1, the number of charges due to the headgroups of the polymeric counterion equals the net number of charges of the ionic surfactant or surfactants comprising the micelles.

IV. Suitable Polymers

Many polymers are suitable for use as polymeric counterions in the instant invention. In one embodiment, the polymers are water-soluble as defined herein. The polymers may be homopolymers or copolymers, and they may be linear or branched. Linear polymers may be preferred in at least some embodiments. Copolymers may be synthesized by processes expected to lead to statistically random or so-called gradient type copolymers. In contrast, water-soluble block copolymers are not suitable, since these types of polymers may form aggregates or micelles, in which the more hydrophobic block or blocks comprise the core of the aggregates or micelles and the more hydrophilic block comprises a "corona" region in contact with water. It is thought that these self-assembly processes compete with the electrostatic interactions required for a water-soluble polymer to serve as a polymeric counterion with ordinary surfactant micelles. Although mixtures of water-soluble polymers are suitable in at least some embodiments of the present invention, the mixtures selected should not comprise block copolymers capable of forming so-called "complex coacervate" micelles through self-assembly, since this micelle formation process also competes with the interaction of the water-soluble polymer as a polymeric counterion to ordinary surfactant micelles. When the polymers are copolymers, the ratio of the two or more monomers may vary over a wide range, as long as water solubility of the polymer is maintained.

In an embodiment, the polymers should be water soluble, as defined herein, and therefore, should not be latex particles or microgels of any type. In such embodiments the polymers should not be cross-linked through the use of monomers capable of forming covalent bonds between independent polymer chains, and the compositions and formulations should be free of cross-linking agents added expressly for this purpose. It is believed that polymer aggregates that may be "swollen" by water in the form of microgels or polymers that form cross-linked networks will not have the appropriate full mobility of the polymer chains needed for them to function as polymeric counterions with respect to ordinary surfactant micelles. Polymer particles which can serve as structurants for an aqueous composition through the formation of fibers or threads are not suitable as the water-soluble polymers for similar reasons. Similarly, latex particles are believed to not be suitable because many of the individual polymer chains in such particles are, in fact, confined to the particle interior and are not readily available for interaction with the aqueous phase. Latex particles also lack the chain mobility required to function as counterions to ordinary surfactant micelles.

The random copolymers may comprise one or more monomers bearing the same charge or capable of developing the same charge and one or more monomers which are nonionic, i.e., not capable of bearing a charge. Copolymers may be synthesized by graft processes, resulting in "comb-like" structures.

Preferred copolymers include so-called "hybrid" materials from Akzo Nobel such as Alcoguard® H 5240. These materials are described as comprising polysaccharides and synthetic monomers which can function in the same manner as acrylate/maleate copolymers (i.e., a water-soluble polymer with anionically charged groups) in cleaning formulations. Hybrid polymers such as those described in U.S. Pat. No. 8,058,837 are preferred in formulations where the overall sustainability of the formulation is of concern to the end user. Such hybrid polymers are derived from synthetic monomers chain terminated with a hydroxyl-containing natural material, such as a polysaccharide, using free radical initiators.

Various anionic polymers available from Akzo Nobel under the tradenames Alcoguard®, Alcosperse®, and Aquatreat® are suitable for use. For example, Alcosperse® 747, a random copolymer. Aquatreat® AR-4, an acrylic acid homopolymer, and Alcoguard® 5240, a random graft copolymer, all of which contain carboxylic acid groups, are additional examples of anionic polymers that may be employed. Alcoguard® 2300 is a random copolymer of the nonionic monomer dimethylacrylamide and the anionic monomer acrylic acid. Alcosperse® 465 is a poly(acrylic acid) homopolymer. Versa-TL® 4 (Akzo Nobel) is another example of a suitable anionic polymer. This material is described as a random copolymer of sulfonated styrene and maleic anhydride. Another example of a suitable anionic polymer is poly(2-acrylamido-2-methyl-1-propanesulfonic acid), also known as polyAMPS.

In one embodiment, the compositions are free of copolymers comprising at least one monomer bearing or capable of developing an anionic charge and at least one monomer bearing or capable of developing a cationic charge. Such copolymers, sometimes referred to as "amphoteric" copolymers, are believed to not function as well or at all as polymeric counterions to micelles bearing a net electrostatic charge for at least two reasons. First, the proximity of both types (anionic and cationic) of charges along the polymer chains, if randomly distributed, interferes with the efficient pairing of a given type of charge on the polymer chain with the headgroup of a surfactant of opposite charge in a micelle. Second, such copolymers have the potential for electrostatic interactions of the anionic charges on a given polymer chain with the cationic charges on another polymer chain. Such interactions could lead to the formation of polymer aggregates or complexes in a process that is undesirably competitive with the interaction of the polymer with micellar aggregates.

The water-soluble polymers may include natural or sustainable materials bearing anionic groups, including inulin derivatives (example Carboxyline CMI or Dequest PB), anionically modified starches with the proviso that they exhibit water solubility without cooking to achieve water solubility, water-soluble salts of alginic acids, anionically modified cellulosic materials such as carboxymethyl cellulose, modified proteins, and the like Non-limiting examples of monomers bearing or capable of bearing an anionic charge are acrylic acid, methacrylic acid, vinyl sulfonate, acrylamido propyl methane sulfonic acid (AMPS), itaconic acid, maleic acid, fumaric acid, phthalic acid, iso-phthalic acid, pyromellitic acid, methallyl sulfonate, sulfonated styrene, crotonic acid, aconitic acid, cyanoacrylic acid, methylene malonic acid, vinyl acetic acid, allyl acetic acid, ethylidineacetic acid, propylidineacetic acid, angelic acid, cinnamic acid, styrylacrylic acid, citraconic acid, glutaconic acid, phenylacrylic acid, acryloxyproprionic acid, vinyl benzoic acid, N-vinylsuccinamide acid, mesaconic acid, methacroyl alanine, acrylohydroxyglycine, sulfoethyl acrylate, styrene sulfonic acid, 3-(vinyloxy)propane-1-sulfonic acid, ethyelenesultbnic acid, vinyl sulfuric acid, 4-vinylphenyl sulfuric acid, vinyl phosphonic acid, maleic anhydride, and mixtures thereof. Suitable monomers may include acid-functional ethylenically unsaturated monomers capable of polymerization or copolymerization via processes including free radical polymerization, ATRP and RAFT polymerization conditions that are expected to produce statistically random or gradient copolymers with ethylenically unsaturated monomers which are incapable of developing a charge, the so-called nonionic monomers.

Non-limiting examples of monomers which are nonionic, not bearing, or not capable of bearing an electrostatic charge include the alkyl esters of acrylic acid or methacrylic acid, vinyl alcohol, vinyl methyl ether, vinyl ethyl ether, ethylene oxide, propylene oxide, and mixtures thereof. Other examples include acrylamide, dimethylacrylamide, and other alkyl acrylamide derivatives. Other suitable monomers may include ethoxylated esters of acrylic acid or methacrylic acid, the related tristyryl phenol ethoxylated esters of acrylic acid, methacrylic acid or mixtures thereof. Other examples of nonionic monomers include saccharides such as hexoses and pentoses, ethylene glycol, alkylene glycols, branched polyols, and mixtures thereof.

In some embodiments, water-soluble polymers comprising monomers which bear N-halo groups, for example, N—Cl groups, are not present. It is believed that interactions between polymers comprising such groups as polymeric counterions to micelles leads to either a degradation of the surfactants themselves and/or a degradation of the polymers through the enhanced local concentration of the polymers at the micelle surfaces.

When the compositions comprise surfactant micelles with, for example, a net cationic charge and a water-soluble polymer or mixture of polymers bearing or capable of bearing anionic charges, then the compositions may be free of any additional polymers bearing a cationic charge. i.e., a charge opposite to that of the first water-soluble polymer bearing or capable of bearing anionic charges. The presence of a first water-soluble polymer bearing an anionic charge and a second water-soluble polymer bearing a cationic charge in the same formulation is believed to give rise to the formation of complexes between the two polymers, i.e., so-called polyelectrolyte complexes, which would undesirably compete with the formation of complexes between the micelles bearing the cationic charge and the polymer bearing the anionic charge.

However, compositions comprising surfactant micelles bearing a net electrostatic charge and a water-soluble polymer bearing or capable of bearing an electrostatic charge opposite to that of the surfactant micelles may comprise additional polymers which do not bear charges, that is, nonionic polymers. Such nonionic polymers may be useful as adjuvants for thickening, gelling, or adjusting the rheological properties of the compositions or for adjusting the aesthetic appearance of the formulations through the addition of pigments or other suspended particulates. It should be noted, however, that in many cases, the polymer-micelle complexes of the instant invention, when adjusted to certain total actives concentrations, may exhibit "self-thickening" properties and not explicitly require an additional polymeric thickener, which is desirable from a cost standpoint.

V. Suitable Surfactants

In one embodiment, the compositions are free of nonionic surfactants which comprise blocks of hydrophobic and hydrophilic groups, such as the Pluronics®. It is believed that the micellar structures formed with such large surfactants, in which the hydrophobic blocks assemble into the core regions of the micelles and the hydrophilic blocks are present at the micellar surface would interfere with the polymeric counterion interactions with an additional charged surfactant incorporated into a mixed micelle, and/or also represent a more competitive micelle assembly mechanism, in a manner similar to that of the use of block copolymers used as polymeric counterions, which are also preferably not present.

A very wide range of surfactants and mixtures of surfactants may be used, including anionic, nonionic and cationic surfactants and mixtures thereof. As alluded to above in the description of Dnet and P/Dnet, it will be apparent that mixtures of differently charged surfactants may be employed. For example, mixtures of cationic and anionic surfactants, mixtures of cationic and nonionic, mixtures of anionic and nonionic, and mixtures of cationic, nonionic and anionic may be suitable for use.

Examples of cationic surfactants include, but are not limited to monomeric quaternary ammonium compounds, monomeric biguanide compounds, and combinations thereof. Suitable exemplary quaternary ammonium compounds are available from Stepan Co under the tradename BTC® (e.g., BTC® 1010, BTC® 1210, BTC®, 818, BTC® 8358). Any other suitable monomeric quaternary ammonium compound may also be employed. BTC® 1010 and BTC® 1210 are described as didecyl dimethyl ammonium chloride and a mixture didecyl dimethyl ammonium chloride and n-alkyl dimethyl benzyl ammonium chloride, respectively. Examples of monomeric biguanide compounds include, but are not limited to chlorhexidine, alexidine and salts thereof.

Examples of anionic surfactants include, but are not limited to alkyl sulfates, alkyl sulfonates, alkyl ethoxysulfates, fatty acids and fatty acid salts, linear alkylbenzene sulfonates (LAS and HLAS), secondary alkane sulfonates (for example Hostapur® SAS-30), methyl ester sulfonates (such as Stepan-Mild® PCL from Stepan Corp), alkyl sulfosuccinates, and alkyl amino acid derivatives. Rhamnolipids bearing anionic charges may also be used, for example, in formulations emphasizing greater sustainability, since they are not derived from petroleum-based materials. An example of such a rhamnolipid is JBR 425, which is supplied as an aqueous solution with 25% actives, from Jenil Biosurtactant Co., LLC (Saukville, Wis., USA).

So-called "extended chain surfactants", are preferred in some formulations. Examples of these anionic surfactants are described in US Pat. Pub. No. 2006/0211593.

Non-limiting examples of nonionic surfactants include alkyl amine oxides (for example Ammonyx® LO from Stepan Corp.) alkyl amidoamine oxides (for example Ammonyx® LMDO from Stepan Corp.), alkyl phosphine oxides, alkyl polyglucosides and alkyl polypentosides, alkyl poly (glycerol esters) and alkyl poly(glycerol ethers), and alkyl and alkyl phenol ethoxylates of all types and mixtures thereof. Sorbitan esters and ethoxylated sorbitan esters are also useful nonionic surfactants. Other useful nonionic surfactants include, but are not limited to, fatty acid amides, fatty acid monoethanolamides, fatty acid diethanolamides, and fatty acid isopropanolamides.

In one embodiment, a phospholipid surfactant may be included. Lecithin is an example of a phospholipid.

In one embodiment, synthetic zwitterionic surfactants may be present. Non-limiting examples include N-alkyl betaines (for example Amphosol®, LB from Stepan Corp.), alkyl sulfo-betaines and mixtures thereof.

In one embodiment, at least some of the surfactants may be edible, so long as they exhibit water solubility or can form mixed micelles with edible nonionic surfactants. Non-limiting examples of such edible surfactants include casein or lecithin or mixtures thereof.

In one embodiment, the surfactants may be selected based on green or natural criteria. For example, there is an increasing desire to employ components that are naturally-derived, naturally-processed, and biodegradable, rather than simply being recognized as safe. For example, processes such as ethoxylation may be undesirable where it is desired to provide a green or natural product, as such processes can leave residual compounds or impurities behind. Such "natural surfactants" may be produced using processes perceived to be more natural or ecological, such as distillation, condensation, extraction, steam distillation, pressure cooking and hydrolysis to maximize the purity of natural ingredients. Examples of such "natural surfactants" that may be suitable for use are described in U.S. Pat. Nos. 7,608,573, 7,618,931, 7,629,305, 7,939,486, 7,939,488, all of which are herein incorporated by reference.

VI. Suitable Adjuvants

A wide range of optional adjuvant or mixtures of optional adjuvants may be present. For example, builders and chelating agents, including but not limited to EDTA salts, GLDA, MSG, gluconates, 2-hydroxyacids and derivatives, glutamic acid and derivatives, trimethylglycine, etc. may be included.

Amino acids and mixtures of amino acids may be present, as either racemic mixtures or as individual components of a single chirality.

Vitamins or vitamin precursors, for example retinal, may be present.

Sources of soluble zinc, copper, or silver ions may be present, as the simple inorganic salts or salts of chelating agents, including, but not limited to, EDTA, GLDA, MGDA, citric acid, etc.

Dyes and colorants may be present. Polymeric thickeners, when used as taught above, may be present.

Buffers, including but not limited to, carbonate, phosphate, silicates, borates, and combinations thereof may be present. Electrolytes such as alkali metal salts, for example including, but not limited to, chloride salts (e.g., sodium chloride, potassium chloride), bromide salts, iodide salts, or combinations thereof may be present.

Water-miscible solvents may be present in some embodiments. Lower alcohols (e.g., ethanol), ethylene glycol, propylene glycol, glycol ethers, and mixtures thereof with water miscibility at 25° C. may be present in some embodiments. Other embodiments will include no lower alcohol or glycol ether solvents. Where such solvents are present, some embodiments may include them in only small amounts, for example, of not more than 5% by weight, not more than 3% by weight, or not more than 2% by weight.

Water-immiscible solvents may be present, being solubilized into the micelles.

Water-immiscible oils may be present, being solubilized into the micelles. Among these oils are those added as fragrances. Preferred oils are those that are from naturally derived sources, including the wide variety of so-called essential oils derived from a variety of botanical sources. Formulations intended to provide antimicrobial benefits, coupled with improved overall sustainability may advantageously comprise quaternary ammonium compounds or water soluble salts of chlorhexidine or alexidine in combination with essential oils such as thymol and the like, preferably in the absence of water-miscible alcohols.

In one embodiment, the composition may further include one or more oxidants. Examples of oxidants include, but are not limited to hypohalous acid, hypohalite and sources thereof (e.g., alkaline metal salt and/or alkaline earth metal salt of hypochlorous or hypobromous acid), hydrogen peroxide and sources thereof (e.g., aqueous hydrogen peroxide, perborate and its salts, percarbonate and its salts, carbamide peroxide, metal peroxides, or combinations thereof), peracids, peroxyacids, peroxoacids (e.g. peracetic acid, percitric acid, diperoxydodecanoic acid, peroxy amido phthalamide, peroxomonosulfonic acid, or peroxodisulfamic acid) and sources thereof (e.g. salts (e.g., alkali metal salts) of peracids or salts of peroxyacids such as peracetic acid, percitric acid, diperoxydodecanoic acid sodium potassium peroxysulfate, or combinations thereof), organic peroxides and hydroperoxides (e.g. benzoyl peroxide) peroxygenated inorganic compounds (e.g. perchlorate and its salts, permanganate and its salts and periodic acid and its salts), solubilized chlorine, solubilized chlorine dioxide, a source of free chlorine, acidic sodium chlorite, an active chlorine generating compound, or a chlorine-dioxide generating compound, an active oxygen generating compound, solubilized ozone, N-halo compounds, or combinations of any such oxidants. Additional examples of such oxidants are disclosed in U.S. Pat. No. 7,517,568 and U.S. Publication No. 2011/0236582, each of which is herein incorporated by reference in its entirety.

Water-soluble hydrotropes, sometimes referred to as monomeric organic electrolytes, may also be present. Examples include xylene sulfonate salts, naphthalene sulfonate salts, and cumene sulfonate salts.

Enzymes may be present, particularly when the formulations are tuned for use as laundry detergents or as cleaners for kitchen and restaurant surfaces, or as drain openers or drain maintenance products.

Applicants have found that a wide range surfactant mixtures resulting in a wide range of Dnet values may be used. In many cases, the surfactants selected may be optimized for the solubilization of various water-immiscible materials, such as fragrance oils, solvents, or even the oily soil to be removed from a surface with a cleaning operation. In the cases of the design of products which deliver an antimicrobial benefit in the absence of a strong oxidant such as hypochlorite, a germicidal quaternary ammonium compound or a salt of a monomeric biguanide such as chlorhexidine or alexidine are often incorporated, and hence are incorporated into micelles with polymeric counterions. The fine control over the spacing between the cationic headgroups of the germicidal quaternary ammonium compound or biguanide which is achieved via the incorporation of a polymeric counterion can result in a significant reduction in the amount of surfactant needed to solubilize an oil, resulting in cost reductions and improvement in the overall sustainability of the formulations.

In contrast to what is described in the art, applicants have also found that the magnitude and precise value of P/Dnet needed to ensure the absence of precipitates and/or coacervate phases can vary widely, depending on the nature of the polymeric counterion and the surfactants selected to form the mixed micelles. Thus, since there is great flexibility in the selection of the polymeric counterion for a given surfactant mixture to achieve a particular goal, applicants have adopted a systematic, but simple approach for quickly "scanning through" ranges of P/Dnet, in order to identify, and to compare, formulations comprising polymeric counterions.

The formulations comprising the mixed micelles of a net charge and a water-soluble polymer bearing charges opposite to that of the micelles are useful as ready to use surface cleaners delivered via pre-moistened nonwoven substrates (e.g., wipes), or as sprays in a variety of packages familiar to consumers.

Concentrated forms of the formulations may also be developed which may be diluted by the consumer to provide solutions that are then used. Concentrated forms that suitable for dilution via automated systems, in which the concentrate is diluted with water, or in which two solutions are combined in a given ratio to provide the final use formulation are possible.

The formulations may be in the form of gels delivered to a reservoir or surface with a dispensing device. They may optionally be delivered in single-use pouches comprising a soluble film.

The superior wetting, spreading, and cleaning performance of the systems make them especially suitable for delivery from aerosol packages comprising either single or dual chambers.

When the compositions comprise chlorhexidine or alexidine salts as a cationically charged surfactant, the compositions may be free of iodine or iodine-polymer complexes, nanoparticles of silver, copper or zinc, triclosan, p-chloromethyl xylenol, monomeric pentose alcohols, D-xylitol and its isomers, D-arabitol and its isomers, aryl alcohols, benzyl alcohol, and phenoxyethanol.

VII. Suitable Nonwoven Substrates

Many of the compositions are useful as liquids or lotions that may be used in combination with nonwoven substrates to produce pre-moistened wipes. Such wipes may be employed as disinfecting wipes or for floor cleaning in combination with various tools configured to attach to the wipe.

In one embodiment, the cleaning pad of the present invention comprises a nonwoven substrate or web. The cleaning substrates can be provided dry, pre-moistened, or impregnated with cleaning composition, but dry-to-the-touch. In one aspect, dry cleaning substrates can be provided with dry or substantially dry cleaning or disinfecting agents coated on or in the multicomponent multilobal fiber layer. In addition, the cleaning substrates can be provided in a pre-moistened and/or saturated condition. The wet cleaning substrates can be maintained over time in a sealable container such as, for example, within a bucket with an attachable lid, sealable plastic pouches or bags, canisters, jars, tubs and so forth.

VIII. Examples

How Particle Size and Zeta Potentials were Measured

The diameters of the aggregates with the polymeric counterions (in nanometers) and their zeta potentials were measured with a Zetasizer ZS (Malvern Instruments). This instrument utilizes dynamic light scattering (DLS, also known as Photon Correlation spectroscopy) to determine the diameters of colloidal particles in the range from 0.1 to 10000 nm.

The Zetasizer ZS instrument offers a range of default parameters which can be used in the calculation of particle diameters from the raw data (known as the correlation function or autocorrelation function). The diameters of the aggregates reported herein used a simple calculation model, in which the optical properties of the aggregates were assumed to be similar to spherical particles of polystyrene latex particles, a common calibration standard used for more complex DLS experiments. In addition, the software package supplied with the Zetasizer provides automated analysis of the quality of the measurements made, in the form of "Expert Advice". The diameters described herein (specifically what is known as the "Z" average particle diameter) were calculated from raw data that met "Expert Advice" standards consistent with acceptable results, unless otherwise noted. In other words, the simplest set of default measurement conditions and calculation parameters were used to calculate the diameters of all of the aggregates described herein, in order to facilitate direct comparison of aggregates based on a variety of polymeric counterions and surfactants, and avoiding the use of complex models of the scattering which could complicate or prevent comparisons of the diameters of particles of differing chemical composition. Those skilled in the art will appreciate the particularly simple approach taken here, and realize that it is useful in comparing and characterizing complexes of micelles and water-soluble polymers, independent of the details of the types of polymers and surfactants utilized to form the complexes.

This instrument calculates the zeta potential of colloidal particles from measurements of the electrophoretic mobility, determined via a Doppler laser velocity measurement. There exists a relationship between the electrophoretic mobility (a measurement of the velocity of a charged colloidal particle moving in an electric field) and the zeta potential (electric charge, expressed in units of millivolts). As in the particle size measurements, to facilitate direct comparison of aggregates based on a variety of polymeric counterions and surfactants, the simplest set of default measurement conditions were used, i.e., the aggregates were assumed to behave as polystyrene latex particles, and the Smoluchowski model relating the electrophoretic mobility and the zeta potential was used in all calculations. Unless otherwise noted, the mean zeta potentials described herein were calculated from raw data that met "Expert Advice" standards consistent with acceptable results. Aggregates bearing a net cationic (positive) charge will exhibit positive values of the zeta potential (in mV), while those bearing a net anionic (negative) charge will exhibit negative values of the zeta potential (in mV).

Example 1

Ready to Use Disinfecting Spray Cleaner Formulation Mean Diameter and Zeta Potential of Surfactant Micelles with and without Polymeric Counterion The interaction between mixed micelles comprising an amine oxide and two different germicidal quaternary ammonium compounds and an anionic polymeric counterion can be readily illustrated by comparing the diameters of the mixed micelles (as measured by DLS) in the absence and presence of the polymeric counterion. The aqueous control formulations were prepared by mixing the germicidal quaternary ammonium raw material (supplied as aqueous solutions, Stepan Corp.) with the amine oxide raw material (supplied as an aqueous solution, Stepan Corp.) to form a mixed surfactant stock solution. Appropriate amounts of the surfactant stock solution, monoethanolamine (to adjust pH above 9.0) and water were mixed to form the final control formulation containing the mixed micelles. In the case of the formulations comprising the polymeric counterion, the same mixed surfactant stock solution, monoethanolamine, Alcosperse® 747 (supplied as an aqueous solution, Akzo Nobel), and water were mixed in appropriate amounts to yield the final formulations with different P/Dnet values, but with the same mixed micelle compositions. The formulations, all of which were clear solutions free of coacervate or precipitates, are summarized in Table 1.1. The measured values of the Z-average diameters and the zeta potentials of the aggregates are summarized in Table 1.2.

TABLE 1.2

| Formulation Name | P/Dnet | Z average diameter, nm | Mean zeta potential, mV | Comments |
|---|---|---|---|---|
| A1 | 0 | 1.032 | +36.6 | Micellar aggregate control |
| A2 | 0 | 1.006 | +32.6 | Micellar aggregate control |
| A3 | −0.1 | 76.08 | +56.8 | With polymeric counterion |
| A4 | −0.25 | 83.19 | +51.8 | With polymeric counterion |
| A5 | −0.1 | 79.14 | +50.0 | With polymeric counterion |
| A6 | −0.25 | 92.57 | +50.5 | With polymeric counterion |

The results in Table 1.2 indicate that the micellar aggregate controls at P/Dnet=0 were around 1 nm in diameter, which is an expected size range for micellar aggregates of ionic surfactants in aqueous solutions. These results suggest that the default parameters selected for calculation of the diameters from the DLS measurements, as described above, were reasonable, and thus could be used for comparing changes in diameter due to the interactions between the micellar aggregates and the polymeric counterions.

Since these aggregates comprised mixed micelles of an amine oxide surfactant, which is expected to be uncharged at the high pH of the formulation and a cationic germicidal quat, a positive mean zeta potential is expected and is observed for the two control systems comprising the two distinct germicidal quaternary ammonium compounds.

The addition of the water-soluble anionic polymer Alcosperse 747 to the formulations at P/Dnet values of −0.1 and −0.25 yielded clear solutions that were free of coacervate. The strong electrostatic interactions between the polymer and the mixed micelles result in the formation of stable aggregates that are much larger in average diameter than the micellar controls, but which are still small enough to exhibit colloidal stability and a clear appearance. Increasing the absolute value of P/Dnet from 0.1 to 0.25 corresponds to moving closer to the lower boundary of the coacervate region for mixed micelles of this composition and at this total surfactant concentration, and hence the average diameters measured increase somewhat.

In order to test whether these larger aggregates comprising mixed micelles and the polymeric counterion were stable structures, repeated measurements of the aggregate diameters were made on undisturbed samples held in cuvettes in the instrument, every 5 minutes over the course of about one hour. Thus, any growth in the aggregates, which might be a precursor to coacervate or precipitate formation and which would be less obvious than the haziness of samples detected visually,

TABLE 1.1

| Formulation Name | Polymer Alcosperse ® 747 wt % | Amine Oxide, Ammonyx ® LO, wt % | Germicidal Quat, BTC ® 1010, wt % | Germicidal Quat, BTC ® 1210, wt % | Monoethanolamine wt % | P/Dnet | Dnet |
|---|---|---|---|---|---|---|---|
| A1 | | 0.23 | 0.36 | | 0.1 | 0 | 0.000994 |
| A2 | | 0.23 | — | 0.36 | 0.1 | 0 | 0.0010 |
| A3 | 0.02 | 0.23 | 0.36 | — | 0.1 | −0.1 | 0.000994 |
| A4 | 0.05 | 0.23 | 0.36 | — | 0.1 | −0.25 | 0.000994 |
| A5 | 0.02 | 0.23 | — | 0.36 | 0.1 | −0.1 | 0.001 |
| A6 | 0.05 | 0.23 | — | 0.36 | 0.1 | −0.25 | 0.001 |

Alcosperse® 747 (Akzo Nobel) acrylic acid:styrene random copolymer supplied as aqueous solution (40% actives) with Z=−1 and Eq polymer=0.005054 equivalents/gram of polymer actives.

BTC® 1010 quaternary ammonium germicide (Stepan Co.) supplied as aqueous solution (80% actives) described as didecyl dimethyl ammonium chloride, average molecular weight=362 grams/mole, Q=1.

BTC® 1210 quaternary ammonium germicide (Stepan Co.) supplied as aqueous solution (80% actives) described as a mixture of didecyl dimethyl ammonium chloride and n-alkyl (50% C14, 40% C12, 10% C16) dimethyl benzyl ammonium chloride, average molecular weight=360.5 grams/mole, Q=1.

would be detectable from a trend in the Z-average diameters over time. No such trends were detected for samples A3 through A6. All of these samples exhibited relative standard deviations of the Z-average diameters of less than 1% from the 11 sequential measurements made. The Z-average diameters for these samples, based on 11 measurements each, are those reported in Table 1.2.

Since the aggregates with the polymeric counterions were formulated at an absolute value of P/Dnet<1.0, the number of cationic charges provided by the germicidal quaternary ammonium compound in the mixed micelles exceeds that of the anionic charges provided by the anionic polymer, and the stable colloidal aggregates formed would be expected to bear a net cationic charge and hence a positive zeta potential. Table 1.2 shows that the aggregates formed with the polymeric counterion have mean zeta potential values that are positive, even somewhat greater than the micelles alone, consistent with the formation of distinct, tunable aggregates which cannot be formed without the use of a polymeric counterion, that is, that cannot be formed at the same total surfactant concentration and the same mixed micelle compositions when the native counterions of the cationic surfactant (the germicidal quaternary ammonium compound), here chloride ions, are the only ones present. A conservative estimate of the precision of all of the zeta potential measurements referenced herein is about 10% of the reported mean value.

Example 2

Ready to Use Disinfecting Cleaner Lotion Suitable for Delivery from a Nonwoven Wipe Mean Diameter and Zeta Potential of Surfactant Micelles without and with Polymeric Counterion

At Low Y Values

A series of formulations were prepared in the same manner as in Example 1, at a lower relative concentration of the germicidal quaternary ammonium compound in the mixed surfactant aggregates. Formulations using these mixed micelle compositions are suitable for use as lotions which can be loaded onto nonwoven wipes and provide convenient disinfection of hard surfaces combined with good cleaning of greasy soils, all without the requirement for the addition of volatile organic solvents such as lower alcohols or glycol ethers. The formulations comprising the polymeric counterion were clear and free of coacervate when the absolute value of P/Dnet was less than 0.30, according to an inspection of a series of samples covering a range of this parameter between 0 and 0.5 at this total surfactant concentration and micelle composition.

TABLE 2.1

| Formulation Name | Polymer Alcosperse ® 747 wt % | Amine Oxide, Ammonyx ® LO, wt % | Germicidal Quat, BTC ® 1010, wt % | Germicidal Quat, BTC ® 1210, wt % | Monoethanolamine wt % | P/Dnet | Dnet parameter |
|---|---|---|---|---|---|---|---|
| A7 | — | 2.05 | 0.36 | | 0.1 | 0 | +0.000994 |
| A8 | — | 2.05 | — | 0.36 | 0.1 | 0 | +0.001 |
| A9 | 0.002 | 2.05 | 0.36 | — | 0.1 | −0.01 | +0.000994 |
| A10 | 0.02 | 2.05 | 0.36 | — | 0.1 | −0.1 | +0.000994 |
| A11 | 0.02 | 2.05 | — | 0.36 | 0.1 | −0.1 | +0.001 |
| A12 | 0.05 | 2.05 | — | 0.36 | 0.1 | −0.25 | +0.001 |

TABLE 2.2

| Formulation Name | P/Dnet | Z average diameter, nm | Mean zeta potential, mV | Comments |
|---|---|---|---|---|
| A7 | 0 | 2.505 (n = 5, 2 preps) | +6.91 | Micellar aggregate control |
| A8 | 0 | 2.417 (n = 6, 2 preps) | Not measured | Micellar aggregate control |
| A9 | −0.01 | 3.266 (n = 3) | +9.31 | With polymeric counterion |
| A10 | −0.1 | 3.298 (n = 3) | +7.99 | With polymeric counterion |
| A11 | −0.1 | 3.114 (n = 3) | +4.18 | With polymeric counterion |
| A12 | −0.25 | 3.680 (n = 3) | +4.69 | With polymeric counterion |

The results in Table 2.2 show that, at this total surfactant concentration and mixed micelle composition, the mixed micelles are somewhat larger than those formulated with the same quaternary ammonium compound and amine oxide as shown in Table 1.1. Without being bound by theory, it is believed that as the relative amount of quaternary ammonium compound in the mixed micelles decreases, an effective dilution of the charged quaternary ammonium compound headgroups in the micelles occurs due to the additional numbers of amine oxide molecules, which allows greater average spacing between the charged quaternary ammonium compound headgroups and a growth in the average micelle diameter. Also, due to the lower average number of quaternary ammonium compound molecules present in the mixed aggregates, the measured mean zeta potential is reduced, but is confirmed to be positive, i.e., cationic, as expected.

The results in Table 2.2 also indicate that the addition of an anionic polymeric counterion at P/Dnet values that do not cause formation of coacervates results in aggregates which are significantly larger than the micellar controls, but still small enough to exhibit colloidal stability. The relative standard deviations of the measured Z-average diameters of each of the formulations were again found to be less than 1.0%, even when multiple preparations of the same compositions were prepared on different days, and hence the differences in diameter between the control formulations and those comprising the polymeric counterions may be considered detectable and significant.

The results in Table 2.2 also indicate that the aggregates formed with the addition of the anionic polymeric counterion, at absolute values of P/Dnet less than 1.0, exhibit a positive (cationic) zeta potential, as expected.

Thus, the addition of a polymeric counterion yields stable, soluble aggregates with a tunable size and charge which can be adjusted through the mixed micelle composition and the P/Dnet value. As shown elsewhere herein, such aggregates exhibit surprisingly good antimicrobial performance, across a range of microorganisms, without requiring volatile organic materials such as alcohols or glycol ethers to boost or "potentiate" the action of the quaternary ammonium compound. It is believed, without being bound by theory, that the aggregates comprising polymeric counterions can more readily act at the solid-liquid interface, including that of microbes, enhancing the delivery of the germicidal quaternary ammonium compound and thus enhancing antimicrobial efficacy.

Example 3

Ready to Use Disinfecting Cleaner Lotion Suitable for Delivery from a Nonwoven Wipe Mean Diameter and Zeta Potential of Surfactant Micelles without and with Polymeric Counterion

At Absolute Values of P/Dnet>1

A series of formulations were prepared in the same manner as in Example 1, at a constant mixed micelle composition and Dnet value which are suitable for use as lotions which can be loaded onto nonwoven wipes or used as a ready to use spray cleaner with excellent hard surface wetting properties in the absence of volatile organic solvents such as alcohols or glycol ethers. The formulations comprising the polymeric counterion were clear and free of coacervate at absolute values of P/Dnet greater than 1.3, determined by an inspection of a series of samples covering a wide range of the absolute value of P/Dnet between 0 and 2.0 at the total surfactant concentration. The addition of the anionic polymeric counterions to the mixed micelles containing a quaternary ammonium compound provides a mechanism to tune the solubilization efficiency of water-immiscible oils, through adjustment of both Dnet and the absolute value of P/Dnet.

TABLE 3.1

| Formulation Name | Polymer Alcosperse ® 747 wt % | Amine Oxide, Ammonyx ® LO, wt % | Germicidal Quat, BTC ® 1010, wt % | Limonene, wt % | Monoethanolamine wt % | P/Dnet | Dnet |
|---|---|---|---|---|---|---|---|
| A13 | — | 0.785 | 0.122 | | 0.1 | 0 | +0.000337 |
| A14 | 0.1 | 0.785 | 0.122 | 0.2 | 0.1 | −1.50 | +0.000337 |
| A15 | 0.1 | 0.785 | 0.122 | — | 0.1 | −1.50 | +0.000337 |

TABLE 3.2

| Formulation Name | P/D net | Z average diameter, nm | Mean zeta potential, mV | Comments |
|---|---|---|---|---|
| A13 | 0 | 2.221 | +7.34 | Micellar aggregate control |
| A14 | −1.50 | 9.102 (n = 5) | −2.31 | With polymeric counterion |
| A15 | −1.50 | 9.732 (n = 4, 2 preps) | −11.1 | With polymeric counterion |

The results shown in Table 3.2 show that, at absolute values of P/Dnet greater than 1.0 and outside the region in which coacervates are formed for this system, stable soluble aggregates are formed with the addition of the anionic polymeric counterion. The aggregates have somewhat larger Z-average diameters relative to micellar aggregate controls formed in the absence of the polymeric counterion. Addition of a significant amount of limonene, which is both a model fragrance oil component as well as a model hydrocarbon solvent, to the aggregates comprising the polymeric counterions is readily achieved at the same P/Dnet value as in the absence of the limonene. Thus, the aggregates comprising the mixed surfactant and the polymeric counterion are capable of solubilizing water-insoluble materials such as limonene. It is believed, without being bound by theory, that the solubilization of limonene in the aggregates with the polymeric counterions is possible because the aggregate structures maintain a property of ordinary mixed micelles, i.e., a non-polar interior in which water-insoluble materials may be solubilized, even in the presence of the polymeric counterions.

Example 4

Dilutable Disinfecting Formulations

Z-Average Diameter with and without Polymeric Counterions of Diluted Formulations The addition of polymeric counterions to formulations comprising mixed micelles of a germicidal quaternary ammonium compound and another surfactant provides concentrates which can be diluted either manually or via the use of an automated dilution apparatus to provide economical disinfecting solutions. The enhanced wetting properties of the formulations comprising the polymeric counterions, in the absence of volatile organic materials such as lower alcohols or glycol ethers, provide excellent performance with a minimum of residues, which is of concern, for example, in floor cleaning of health care facilities and the like.

In the first step, the appropriate P/Dnet range for the concentrated formulations was determined, with different germicidal quaternary ammonium compound and an amine oxide surfactant mixture. The concentrates also comprised tetrapotassium ethylenediamine tetraacetate, a common chelant and buffer useful in controlling the effects of common tap water used as a diluent, and NaCl as an electrolyte. Multiple concentrated formulations which were clear and free of coacervate are identified through the adjustment of P/Dnet and NaCl level. Formulations suitable for dilution at a rate of 1:250 by volume are then identified through visual inspection. Formulations which appeared to yield clear, soluble solutions free of coacervate phase when diluted were then analyzed via DLS to confirm that the aggregates comprising polymeric counterions formed by a simple dilution process had diameters in the range expected to provide colloidal stability, i.e., Z-average diameters less than 500 nm, as measured as described herein. The anionic polymeric counterion in these examples is Versa-TL® 4 (Akzo Nobel), described by the supplier as a random copolymer of sulfonated styrene and maleic anhydride, which is supplied as an aqueous solution at 25% actives at pH 7.0, which means the anionic sulfonate groups are present in the salt form, and that the maleic anhydride has been hydrolyzed to maleic acid via reaction with water, and the acid groups are present in the ionized (salt) form. The nominal molecular weight of the polymer is described as 20,000 daltons. The total number of anionically charged groups on this polymer yields 0.006427 moles of anionic groups/gram of polymer solids, and this was used in the calculation of the P/Dnet values listed below.

TABLE 4.1

| Concentrate Formulations at Constant Y = 0.5 | | | | | | | | | |
|---|---|---|---|---|---|---|---|---|---|
| Formulation Name | Polymer Versa-TL ® 4 wt % | Amine Oxide, Ammonyx ® LO, wt % | Germicidal Quat, BTC ® 8358 wt % | Germicidal Quat, BTC ® 1210, wt % | $K_4$ EDTA, wt % | NaCl, wt % | P/Dnet | Clear, stable Concen trate? Y/N | Clear diluted solution? Y/N or — not tested |
| A16 | — | 4.08 | 6.4 | — | 1.0 | 5.0 | 0 | Y | Y |
| A17 | — | 4.07 | — | 6.4 | 1.0 | 5.0 | 0 | Y | Y |
| A18 | 0.137 | 4.08 | 6.4 | — | 1.0 | 5.0 | −0.05 | Y | N |
| A19 | 0.275 | 4.08 | 6.4 | — | 1.0 | 5.0 | −0.10 | Y | N |
| A20 | 0.412 | 4.08 | 6.4 | — | 1.0 | 5.0 | −0.15 | Y | N |
| A21 | 0.550 | 4.08 | 6.4 | — | 1.0 | 5.0 | −0.20 | Y | N |
| A22 | 0.688 | 4.08 | 6.4 | — | 1.0 | 5.0 | −0.25 | Y | N |
| A23 | 1.375 | 4.08 | 6.4 | — | 1.0 | 5.0 | −0.5 | Y | — |
| A24 | 2.75 | 4.08 | 6.4 | — | 1.0 | 5.0 | −1.0 | Y | — |
| A25 | 3.44 | 4.08 | 6.4 | — | 1.0 | 5.0 | −1.25 | N | — |
| A26 | 0.137 | 4.08 | 6.4 | — | — | 5.0 | −0.05 | N | — |
| A27 | 0.275 | 4.08 | 6.4 | — | — | 5.0 | −0.10 | N | — |
| A28 | 0.412 | 4.08 | 6.4 | — | — | 5.0 | −0.15 | N | — |
| A29 | 0.550 | 4.08 | 6.4 | — | — | 5.0 | −0.20 | N | — |
| A30 | 0.068 | 4.07 | — | 6.4 | 1.0 | 5.0 | −0.025 | Y | Y |
| A31 | 0.137 | 4.07 | — | 6.4 | 1.0 | 5.0 | −0.05 | Y | Y |
| A32 | 0.275 | 4.07 | — | 6.4 | 1.0 | 5.0 | −0.10 | Y | N |
| A33 | 0.412 | 4.07 | — | 6.4 | 1.0 | 5.0 | −0.15 | Y | N |
| A34 | 0.550 | 4.07 | — | 6.4 | 1.0 | 5.0 | −0.20 | Y | N |
| A35 | 0.068 | 4.07 | — | 6.4 | — | 5.0 | −0.025 | N | — |
| A36 | 0.137 | 4.07 | — | 6.4 | — | 5.0 | −0.05 | N | — |
| A37 | 0.275 | 4.07 | — | 6.4 | — | 5.0 | −0.10 | N | — |
| A38 | 0.412 | 4.07 | — | 6.4 | — | 5.0 | −0.15 | N | — |
| A39 | 0.550 | 4.07 | — | 6.4 | — | 5.0 | −0.20 | N | — |

The results in Table 4.1 illustrate that multiple concentrate formulations which are clear and free of coacervate (A18 through A24) comprising the anionic polymeric counterion are possible, even up to absolute values of P/Dnet=1.0, when sufficient total electrolyte (NaCl and $K_4$EDTA) is present. Formulations A16 and A17, in which P/Dnet=0 acted as micelle controls. It is believed, without being bound by theory, that the interactions between the polymeric counterion and the mixed micelles comprising quaternary ammonium compound and amine oxide can be adjusted through the addition of ordinary electrolytes like NaCl and $K_4$EDTA, which partially screen the charges on the soluble polymeric counterions from the opposite charges on the mixed micelles, and/or compete with the polymeric counterions for the oppositely charged quaternary ammonium compound molecules in the mixed micelles. When the absolute value of the P/Dnet parameter is at or near 1.0, the number of anionic charges present are exactly or nearly sufficient to completely neutralize the cationic charges due to the germicidal quaternary ammonium compound, which would be expected to lead to the formation of coacervates or precipitates. Surprisingly, however, the absolute value of P/Dnet alone is not a reliable guide for avoiding coacervates or precipitates in the formulations. Instead, for a given desired P/Dnet value, a given mixture of germicidal quaternary ammonium compound and another, uncharged surfactant such as an amine oxide, the concentration of electrolyte or mixture of electrolytes needed to prevent the formation of coacervates or precipitates can be readily, and systematically determined.

Formulations A26 through 29, for example, can be compared with A18 through A21, all of which cover a range of the absolute value of P/Dnet values less than 1.0, which is of interest for lower total actives and hence lower cost. Formulations A26 through A29, have an insufficient total electrolyte level due to the elimination of $K_4$EDTA without an increase in the NaCl concentration, and hence are not clear solutions which would not be suitable candidates for a concentrated formulation.

Similarly, Formulations A30 through A34, in which a different germicidal quaternary ammonium compound is used, are acceptable concentrate candidates. By comparison, formulations A35 through A39, in which the total electrolyte concentration was again reduced via elimination of $K_4$EDTA, are not acceptable concentrate candidates, since none of them were clear solutions, but in fact exhibited cloudiness due to the presence of coacervates and/or precipitates.

In a second step, the behavior upon dilution in water of the stable concentrates was evaluated. A sample of the concentrate (40 microliters) was added to 9.96 ml of water of controlled hardness (representing the 1:250 fold dilution rate of interest for this application) in a capped vial and mixed via manual agitation for a few seconds. The diluted samples were visually evaluated for cloudiness, haziness, or the presence of precipitates immediately. Formulations A30 and A31 are examples of concentrates which, upon dilution, form clear solutions that are free of coacervates or precipitates. DLS was then used to confirm the presence of stable aggregates comprising the mixed micelles and the polymeric counterion, in comparison to mixed micelles comprising the same quaternary ammonium compound and amine oxide surfactant without the polymeric counterion.

TABLE 4.2

| Characterization of Diluted Formulations Prepared from Concentrates | | | | |
|---|---|---|---|---|
| Formulation Name | P/Dnet | Z average diameter, nm | Mean zeta potential, mV | Comments |
| A17 | 0 | 5.141 (n = 4) | +12.5 | Control - no polymeric counterion - diluted in hard water (1:25 dilution)* |
| A31 | −0.05 | 167.7 (n = 5) | +44.5 | With polymeric counterion - diluted 1:250 in hard water - fresh sample* |

TABLE 4.2-continued

Characterization of Diluted Formulations Prepared from Concentrates

| Formulation Name | P/Dnet | Z average diameter, nm | Mean zeta potential, mV | Comments |
|---|---|---|---|---|
| A31 | −0.05 | 178.7 (n = 5) | — | With polymeric counterion - diluted 1:250 in deionized water |
| A30 | −0.025 | 136.8 (n = 5) | — | With polymeric counterion - diluted 1:250 in hard water - fresh sample* |
| A30 | −0.025 | 140.0 (n = 5) | — | With polymeric counterion - diluted 1:250 in hard water - aged 6 hours* |

*Synthetic hard water used for dilution contained calcium and magnesium ions in a 3:1 mole ratio at a total concentration of 150 ppm.

The results in Table 4.2 indicate that the Z-average diameter of the micelles in the control sample is significantly less than that of the formulations comprising the same cationic micelles and the anionic polymeric counterion. It should be noted that successful DLS analysis of the micelle control formulation required that it be diluted only by a factor of 25, in order to ensure an adequate and reproducible level of scattering. The amount of scattering from colloidal particles in the DLS experiment is a function of the average diameter of the particles to the sixth power, or proportional to $(\text{diameter})^6$. Thus, small increases in the average diameter result in very large increases in the amount of scattered light, which in turn allows the detection and analysis of larger particles at much lower concentrations than smaller particles. That expected trend is consistent with the measured diameters of the aggregates formed upon dilution of formulations A30 and A31. The results also indicate that the quality of the water did not have a large effect on the Z-average diameter of the aggregates of formulation 31 formed upon dilution.

In Table 4.2, "fresh sample" means that the first DLS analysis of the diluted sample was conducted within 10 minutes of the initial dilution step. Multiple replicate measurements of the same sample (typically 4 or 5, as indicated) were usually made. Replicates could typically be obtained within 2-3 minutes of each other. The stability of the aggregates formed upon dilution of Formulation A30 was also checked by analyzing the same sample that was allowed to age 6 hours in the instrument. The results indicate that no significant change in the Z average diameter of the aggregates in the diluted sample was observed, indicating that stable structures are formed immediately upon dilution of the concentrates, without need of any special processing other than simple mixing.

The results in Table 4.2 also indicate that the zeta potential of the diluted sample of the control micelles is positive (cationic), as expected. Since the absolute value of P/Dnet for Formulation A31 is 0.05, i.e., significantly less than 1.0, the zeta potential of the stable, soluble aggregates formed upon dilution is expected to be positive (cationic), and the measured result confirms this, at +44.5 mV.

The results in Table 4.1 and 4.2 also indicate that systematic adjustment of the P/Dnet parameter and the electrolyte level (and, if desired, the mixed micelle composition) may be used, with initial visual inspection, to identify concentrates which, upon significant dilution, deliver stable, soluble aggregates comprising mixed micelles of a germicidal quaternary ammonium compound and a second surfactant and an anionic polymeric counterion, in a solution free of coacervates or precipitates.

Example 5

Formulations Suitable for Delivery from Nonwovens

Control of Micelle Interactions with Polymeric Counterions Over Wide Range of P/Dnet The pH of the aqueous formulations comprising mixed micelles with a cationic charge and an anionic polymer may be adjusted over a wide range, providing the polymeric counterion maintains its solubility in water at the pH of interest.

Thus, a series of aqueous formulations in which the pH was adjusted to about pH 7.6 were made in order to confirm the absence of coacervate formation across the P/Dnet range of interest.

Samples were prepared by making the following stock solutions; (1) 0.33 wt % MEA and 0.52 wt % glycolic acid at a pH of 6.9, (2) 1.2 wt % BTC® 1010 and 6.8 wt % Ammonyx®, LO at natural pH, and (3) 1.5 wt % Alcosperse® 747 adjusted to pH 6.2 with glycolic acid. The MEA/glycolic acid stock was then diluted in the proper amount of water followed by addition of the BTC® 1010/Ammonyx® LO stock and finally the Alcosperse® 747 stock. Final pH was measured and found to be between 7.6 and 7.3 for these formulas.

TABLE 5.1

Compositions suitable for delivery from nonwovens

| Formulation Name | BTC ® 1010 wt % | Ammonyx ® LO wt % | Alcosperse ® 747 wt % | MEA wt % | Glycolic acid, wt % | pH |
|---|---|---|---|---|---|---|
| B1 | 0.36 | 2.05 | 0.005 | 0.1 | 0.16 | 7.6 |
| B2 | 0.36 | 2.05 | 0.01 | 0.1 | 0.16 | 7.6 |
| B3 | 0.36 | 2.05 | 0.02 | 0.1 | 0.16 | 7.6 |
| B4 | 0.36 | 2.05 | 0.025 | 0.1 | 0.16 | 7.6 |
| B5 | 0.36 | 2.05 | 0.03 | 0.1 | 0.16 | 7.6 |
| B6 | 0.36 | 2.05 | 0.05 | 0.1 | 0.16 | 7.5 |
| B7 | 0.36 | 2.05 | 0.1 | 0.1 | 0.16 | 7.5 |
| B8 | 0.36 | 2.05 | 0.2 | 0.1 | 0.16 | 7.5 |
| B9 | 0.36 | 2.05 | 0.25 | 0.1 | 0.16 | 7.5 |
| B10 | 0.36 | 2.05 | 0.3 | 0.1 | 0.16 | 7.4 |
| B11 | 0.36 | 2.05 | 0.32 | 0.1 | 0.16 | 7.4 |
| B12 | 0.36 | 2.05 | 0.34 | 0.1 | 0.16 | 7.4 |
| B13 | 0.36 | 2.05 | 0.35 | 0.1 | 0.16 | 7.4 |
| B14 | 0.36 | 2.05 | 0.37 | 0.1 | 0.16 | 7.4 |
| B15 | 0.36 | 2.05 | 0.39 | 0.1 | 0.16 | 7.3 |
| B16 | 0.36 | 2.05 | 0.49 | 0.1 | 0.16 | 7.3 |

TABLE 5.2

Characterization of Cationic Micelles with Anionic Polymeric Counterions at pH 7.3 to pH 7.6

| Formulation Name | P/D net | Z average diameter, nm |
|---|---|---|
| B1 | −0.025 | 2.998 |
| B2 | −0.05 | 3.197 |
| B3 | −0.1 | 3.613 |
| B4 | −0.125 | 3.836 |
| B5 | −0.15 | 4.009 |
| B6 | −0.25 | 5.199 |
| B7 | −0.5 | 7.85 |
| B8 | −1.0 | 12.76 |
| B9 | −1.25 | 23.96 |
| B10 | −1.5 | 26.62 |
| B11 | −1.6 | 29.47 |
| B12 | −1.7 | 20.84 |

TABLE 5.2-continued

| Characterization of Cationic Micelles with Anionic Polymeric Counterions at pH 7.3 to pH 7.6 | | |
|---|---|---|
| Formulation Name | P/D net | Z average diameter, nm |
| B13 | −1.8 | 36.15 |
| B14 | −1.9 | 23.97 |
| B15 | −2.0 | 25.66 |
| B16 | −2.5 | 36.62 |

The visual inspection of the formulations in Table 5.1, comprising cationic mixed micelles and an anionic polymeric counterion indicate that clear, stable solutions were produced across a range of the absolute value of P/Dnet from less than to significantly greater than 1.0. In order to confirm the absence of small amounts of coacervate phase, the Z-average diameters of the series of samples were also measured. The results in Table 5.2 indicate that the binding of the anionic polymeric counterion to the cationic mixed micelles results in aggregates that are all larger than mixed micelles of the same composition without the polymeric counterion. The Z-average diameters of the micelles with polymeric counterions were small enough to exhibit excellent colloidal stability, i.e., the diameters found were <500 nm, and more preferably <100 nm.

Example 6

Stability of Size of Cationic Micelles with Anionic Polymeric Counterions at P/Dnet>1

The absence of coacervate or precipitate phases from formulations comprising micelles with polymeric counterions may, in general, be readily determined by visual examination of samples made on the scale as small as about 10 to 15 ml in capped test tubes. As taught herein, cationic mixed micelles with an anionic polymeric counterion also exhibit the important property of solubilization of water-insoluble oils when coacervate or precipitate phases are absent, and this solubilization may also be evaluated through visual inspection of samples. The absolute value of the P/Dnet parameter cannot be used alone to determine formulations which are free of coacervates or precipitates, but instead must be considered together with the mixed micelle composition and the type of water-soluble polymer selected for use as a polymeric counterion. In order to avoid coacervate and precipitate phases, the polymeric counterion must be soluble in aqueous compositions at the pH of the desired final formulation. The solubility of polymeric counterions in aqueous compositions may also be readily evaluated through visual inspection techniques. Thus, for example, the solubility in water of Alcosperse® 747, a random copolymer, Aquatreat® AR-4, an acrylic acid homopolymer, and Alcoguard® 5240, a random graft copolymer, all of which contain carboxylic acid groups, may be compared over a range of pH values and any polymer which does not exhibit the necessary solubility at the pH of interest may be avoided.

Formulations comprising cationic micelles and anionic polymeric counterions that are free of coacervate and precipitates with the absolute value of the P/Dnet parameter>1 can also be readily identified, for example, formulation B10 in Example 5. In addition to the visual inspection of this sample, which indicated it to be free of coacervates or precipitates, DLS was used to monitor the Z-average diameter of these aggregates upon overnight aging to confirm their stability, i.e., as an alternative method of ensuring that the aggregates remained free of coacervates.

Thus, formulation B10 was placed in a sealed cuvette and a measurement of the Z-average diameter was taken every 30 minutes over a 13.5 hour period, with the temperature controlled at 25° C. Such a procedure may be readily accomplished with the Malvern Zeta Sizer used, and those skilled in the art will realize that equivalent measurements may be made with other instruments. The results of this experiment are shown in Table 6.

TABLE 6

| Z average diameter of Aggregates Comprising Cationic Mixed Micelles and Anionic Polymeric counterion Formulation B10 Stored Overnight | |
|---|---|
| Age of Sample, hours | Z-average diameter, nm |
| 0 | 24.61 |
| 0.5 | 23.95 |
| 1 | 23.61 |
| 1.5 | 23.77 |
| 2 | 23.83 |
| 2.5 | 23.86 |
| 3 | 23.47 |
| 3.5 | 23.66 |
| 4 | 23.71 |
| 4.5 | 23.61 |
| 5 | 24.04 |
| 5.5 | 24.44 |
| 6 | 24.22 |
| 6.5 | 24.35 |
| 7 | 23.83 |
| 7.5 | 23.54 |
| 8 | 23.47 |
| 8.5 | 24.37 |
| 9 | 23.19 |
| 9.5 | 24.33 |
| 10 | 23.67 |
| 10.5 | 24.19 |
| 11 | 23.34 |
| 11.5 | 23.6 |
| 12 | 23.79 |
| 12.5 | 23.8 |
| 13 | 23.97 |
| 13.5 | 25.01 |
| Overall mean Z-average diameter, nm | 23.9 |
| Relative Standard Deviation of Diameter, % | 1.73 |

The results in Table 6 indicate that the Z-average diameter of Formulation B10 appears stable, i.e., with a relative standard deviation of less than 2% over a 13.5 hour period, confirming conclusions made with visual inspection of the sample. The results also indicate that stable formulations free of coacervate and precipitates with the absolute value of P/Dnet>1, comprising cationic micelles and anionic polymeric counterions may be made.

Example 7

Formulations Suitable for Delivery from Nonwovens or as Disinfecting Spray Cleaners Acidic pH Formulations comprising mixed micelles of a germicidal quaternary ammonium compound and an amine oxide may also comprise adjuvants or buffers which can be used to adjust the pH. In these examples, monoethanolamine (MEA) was used to increase the pH of the formulations, and glycolic acid was used to decrease the pH of the formulations. Decreasing the pH of such formulations may be desirable for increasing certain aspects of cleaning performance, for example, the dissolution of hard water spots from sinks, tiles, dishes, etc. The inactivation of certain viruses and bacteria is also known to improve when the pH is decreased below pH 7, to the acid pH range. Certain other aspects of cleaning performance of amine oxides, such as residue deposition on hard surfaces which results in filming or streaking, and decreased ability to solubilize greasy soils tend to be exacerbated as the pH of the formulations is decreased, especially below pH 7. Surprisingly, the use of anionic polymeric counterions in formulations comprising germicidal quaternary ammonium compound and amine oxides improves the wetting properties of the formulations on a range of surfaces, while decreasing residue formation. Thus, the addition of volatile cosolvents to the acidic formulations to improve performance properties may be avoided when polymeric counterions are utilized.

In this example, the water soluble polymer (Alcoguard® 2300 from Akzo Nobel) was a random copolymer of the nonionic monomer dimethylacrylamide (95 mole %) and the anionic monomer acrylic acid (5 mole %), which thus provides 0.00600 moles of anionic groups per gram of polymer actives. This polymer is soluble in water at both low pH, e.g., pH 2.0, and high pH, e.g., pH 10, and can thus be employed as the anionic polymeric counterion to mixed micelles of the germicidal quaternary ammonium compound BTC® 1010 (MW=362 g/mol) and the amine oxide Ammonyx® LO.

Visual inspection and DLS were used to determine the formation of stable aggregates, the compositions of which are summarized in Table 7.1. In Table 7.2, the Z-average diameters are summarized, and indicate the aggregates formed as much larger than mixed micelles of the germicidal quaternary ammonium compound and amine oxide in the absence of the polymeric counterion. P/Dnet was calculated based on characteristics of the polymer and BTC 1010 quaternary ammonium compound.

TABLE 7.1

Compositions

| Formulation Name | BTC ® 1010 wt % | Ammonyx ® LO wt % | Alcoguard ® 2300 wt % | MEA wt % | Glycolic acid, wt % | pH |
|---|---|---|---|---|---|---|
| C1 | 0.36 | 0.23 | 1.17 | 0.1 | 0 | 9.4 |
| C2 | 0.36 | 0.23 | 1.01 | 0.11 | 0 | 9.2 |
| C3 | 0.36 | 0.23 | 1.01 | 0.012 | 0.01 | 4.74 |
| C4 | 0.36 | 0.23 | 0.78 | 0.009 | 0.01 | 4.87 |
| C5 | 0.36 | 0.23 | 0.23 | 0.028 | 0.01 | 5.4 |
| C6 | 0.36 | 0.23 | 1.01 | 3.56 | 0.1 | 9.35 |
| C7 | 0.36 | 0.23 | 1.01 | 0.012 | 0.1 | 4.73 |
| C8 | 0.36 | 0.23 | 0.78 | 0.009 | 0.1 | 4.8 |
| C9 | 0.36 | 0.23 | 0.23 | 0.003 | 0.1 | 5.4 |

TABLE 7.2

Characterization of Compositions

| Formulation Name | P/Dnet | Z average diameter, nm | Comments |
|---|---|---|---|
| C1 | −1.5 | 26.33 | Visually clear |
| C2 | −1.3 | 25.98 | Visually clear |
| C3 | −1.3 | 30.91 | Visually clear |
| C4 | −1.0 | 24.88 | Visually clear |
| C5 | −0.3 | 15.13 | Visually clear |
| C6 | −1.3 | 28.93 | Visually clear |
| C7 | −1.3 | 64.1 | Visually clear |
| C8 | −1.0 | 31.11 | Visually clear |
| C9 | −0.3 | 16.51 | Visually clear |

Example 8

Formulations Suitable for Delivery from Nonwovens or as Disinfecting Spray Cleaners Acidic pH This example shows some additional acidic formulations using mixtures of arginine, an amino acid, and glycolic acid to adjust the pH.

Visual inspection and DLS were used to determine the formation of stable aggregates, the compositions of which are summarized in Table 8.1. In Table 8.2, the Z-average diameters are summarized, and indicate the aggregates formed as much larger than mixed micelles of the germicidal quaternary ammonium compound and amine oxide in the absence of the polymeric counterion. P/Dnet was calculated based on characteristics of the polymer and BTC® 1010 quaternary ammonium compound.

TABLE 8.1

Compositions

| Formulation Name | BTC ® 1010 wt % | Ammonyx ® LO wt % | Alcoguard ® 2300 wt % | Arginine wt % | Glycolic acid, wt % | pH |
|---|---|---|---|---|---|---|
| C10 | 0.37 | 0.23 | 0.088 | 0.174 | 0.08 | 5 |
| C11 | 0.35 | 0.21 | 0.22 | 0.174 | 0.097 | 5 |
| C12 | 0.4 | 0.24 | 0.45 | 0.174 | 0.105 | 5 |
| C13 | 0.34 | 0.21 | 0.67 | 0.174 | 0.112 | 5 |
| C14 | 0.34 | 0.21 | 0.92 | 0.173 | 0.127 | 4.5 |
| C15 | 0.34 | 0.21 | 1.43 | 0.174 | 0.08 | 5 |
| C16 | 0.35 | 0.22 | 1.37 | 0.174 | 0.08 | 5 |
| C17 | 0.34 | 0.22 | 1.55 | 0.174 | 0.08 | 5 |

TABLE 8.2

Characterization of Compositions

| Formulation Name | P/Dnet | Z average diameter, nm | Comments |
|---|---|---|---|
| C10 | −0.1 | 13.51 | Visually clear |
| C11 | −0.25 | 17.15 | Visually clear |
| C12 | −0.5 | 17.56 | Visually clear |
| C13 | −0.75 | 22.91 | Visually clear |
| C14 | −1.0 | 30.79 | Visually clear |
| C15 | −1.95 | 25.78 | Visually clear |
| C16 | −1.8 | 39.41 | Visually clear |
| C17 | −2.12 | 29.31 | Visually clear |

Spores (or more properly, endospores) are a type of dormant cell produced by many types of bacteria, such as *Bacillus* and *Clostridium*, in response to stressful environmental conditions. The exterior coats of spores, which are responsible for the resistance to extreme conditions, are multi-layer structures composed primarily of cross-linked polypeptides. When a spore encounters an environment favorable for growth of vegetative cells, the spore coat also allows access to nutrients and water to the spore, and the production of a vegetative cell, in a germination process.

The compositions of the polypeptides, proteins, and other minor materials that make up the coat of *Bacillus Subtilis* spores, for example, result in the spore exhibiting a net anionic charge (negative zeta potential) when the spores are dispersed in water at neutral pH, i.e., pH 7. Polypeptides in aqueous solutions will exhibit a net charge as a function of pH of the solution that is determined by the relative numbers of anionically and cationically charged amino acids in the polypeptide chain. At a pH corresponding to the isoelectric point of a polypeptide, the net charge on the polypeptide is zero, due to the presence of equal numbers of cationically charged and anionically charged amino acids. The net charge on the polypeptide at pH values greater than the isoelectric point will thus be negative (anionic), and will be positive (cationic) at pH values below the isoelectric point. The isoelectric points (or point of zero charge) of various *Bacillus* spores have been found to lie between about pH 3 and pH 4. Thus, the zeta potential of the spores used herein was found to be cationic (positive) when the spores were dispersed in water adjusted to around pH 2, i.e., well below the known isoelectric point.

*Bacillus* spores exhibit average diameters of around 1000 nm (1 micrometer), and can thus act as charged scattering particles when dispersed in aqueous media. Measurements of the zeta potential of spores are thus readily accomplished using the approach of laser Doppler velocity determination that is implemented in modern instruments, such as the Malvern Zeta Sizer. Those skilled in the art will realize that an appropriate concentration of spores for such measurements of the zeta potential of the spores can readily be determined, using dilutions of standard dispersions of spores which are commercially available. Typically, the spore concentrations in these standard dispersions are expressed as spores/ml or colony forming units/ml of the dispersions. Applicants have found that reproducible measurements of the zeta potential of *Bacillus* spores can easily be made at spore concentrations of around 1 to $3.3\times10^6$ spores/ml. Such concentrations are readily made by dilution of commercially available stocks with concentrations of $1\times10^8$ spores/ml.

Spores contaminating surfaces such as towels, other laundry, or hard surfaces, such as floors, walls, medical equipment, food preparation or service counters, etc. will germinate and grow, producing increasing numbers of organisms on the surface, when the environment becomes favorable, for example, when the surface becomes soiled or contaminated with materials that are suitable nutrients for the microorganisms. Germicidal quaternary ammonium compounds or biguanides have little effect on dormant spores, but if they are present on the surface of the spores in sufficient concentration, they may kill the organism at the initial stage of germination when the environmental conditions otherwise become favorable.

Exposure of spores to solutions comprising micelles with a net cationic charge due to a germicidal quaternary ammonium compound or a monomeric biguanide can result in the adsorption of some quaternary ammonium compound or biguanide onto the spore surface, just as would be the case with any other solid surface, as described above. The amount of adsorption of the quaternary ammonium compound or biguanide will increase as the total concentration of the quaternary ammonium compound or biguanide in solution increases, up to about the critical micelle concentration, at which it will become constant and maximum. The presence of cationic sites (due to cationically charged amino acids and other materials comprising the spore coat) on the spore surface will be expected to oppose and limit the adsorption of cationic quaternary ammonium compound or biguanide.

Adsorption of the quaternary ammonium compound or biguanide will be favored at the anionic sites on the spore surface. If the medium surrounding the spore is suddenly changed, for example by the addition of an organic soil load which could serve as a nutrient source to the spores and thus favor germination, then the adsorbed quaternary ammonium compound or biguanide, like any other surfactant, will re-equilibrate with the surrounding medium, resulting in desorption of at least some of the quaternary ammonium compound or biguanide from the spore surface, thus decreasing its antimicrobial efficacy during the subsequent germination of the spore.

As is shown below, the compositions of the instant invention, in which micelles with a net cationic charge are paired with a water-soluble polymer of anionic charge, while remaining soluble and free of coacervates or precipitates, have the advantage of fine control of the adsorption and desorption of cationic surfactants, including the germicidal quaternary ammonium compound and biguanides, which can be exploited to provide better antimicrobial efficacy against the proliferation of bacteria on surfaces due to the germination of spores.

Example 9

Demonstration of the Adsorption of Germicidal Quaternary Ammonium Compounds onto Spore Surfaces from Mixed Micelles and Mixed Micelles with Polymeric Counterions (Micelle-Polymer Complexes)

The zeta potentials of *Bacillus Subtilis* spores suspended in water at pH 7, the mixed micelles without the polymeric counterion (P/Dnet=0), or mixed micelles interacting with an anionic polymeric counterion were measured using the Malvern Zetasizer. The presence of monoethanolamine in the formulations ensured that the pH was >9.0, which is well above the estimated isoelectric point of the spores, thus ensuring that the spores would exhibit a relatively strongly anionic (negative) zeta potential.

A commercially available stock suspension of *Bacillus Subtilis* spores was used to make all samples on a given day. Samples were analyzed within four hours of preparation. Thirty microliters of the stock spore suspension ($1\times10^8$ cfu/ml) were mixed with 870 microliters of water (pH 7) to give a control sample containing about $3.3\times10^6$ cfu/ml. The entire sample was loaded into a disposable capillary cell for measurement of the zeta potential of the spores, as described generally above. In the case of the formulations, thirty microliters of the stock spore suspension was mixed with 270 μl of the formulation, allowed to equilibrate 10 minutes, and then 600 μl of deionized water was added to again yield a spore suspension of about $3.3\times10^6$ cfu/ml. This sample preparation method was also followed in the comparison of the germicidal activity via the spiral plating method used in the next example below.

TABLE 9.1

| Compositions | | | | | |
|---|---|---|---|---|---|
| Formulation Name | Polymer Alcosperse ® 747 wt % | Amine Oxide, Ammonyx ® LO, wt % | Germicidal Quat, BTC ® 1010, wt % | Monoethanolamine wt % | P/Dnet |
| D1 | 0 | 1.8 | 0.2 | 0.1 | 0 |
| D2 | 0.00255 | 1.8 | 0.2 | 0.1 | −0.05 |
| D3 | 0.102 | 1.8 | 0.2 | 0.1 | −2.0 |

TABLE 9.2

| Zeta potential of *Bacillus Subtilis* spores (3.3 × 10^6 cfu/ml) in water and in Formulations of various P/Dnet | | |
|---|---|---|
| Spore treatment | Absolute value, P/D net | Mean Zeta potential, mV |
| Control - spores only in deionized water | N/A | −46.3 |
| Spores in D1 | 0 | +20.5 |
| Spores in D2 | 0.05 | +12.4 |
| Spores in D3 | 2.0 | −2.9 |

The results in Table 9.2 indicate that the zeta potential of the batch of spores used on this day exhibited an anionic (negative) zeta potential, as expected. Exposure of the spores to formulation D1, the mixed micelles comprising the germicidal quaternary ammonium compound and amine oxide in the absence of a polymeric counterion, causes a large shift in the zeta potential of the spores in the cationic direction, and in fact completely reverses the zeta potential of the spores to +20.5 mV.

This change can be explained by the adsorption of the germicidal quaternary ammonium compound onto the spore surface, causing a compensation of the negatively charged surface sites, which would leave only cationically charged surface sites available to contribute to the zeta potential. It is also possible that overcompensation of the negative sites on the spores could be achieved through the adsorption of multiple layers of quaternary ammonium compound molecules, causing an additional shift in the zeta potential of the spore in the same cationic direction. The results also show that exposure of the spores to formulation D2 results in a shift of the zeta potential in the cationic direction. Since the absolute value of P/Dnet is less than 1.0, the aggregates (complexes) formed by the interaction of the polymeric counterion and the mixed micelles have the cationic charges due to the quaternary ammonium compound in excess, and thus have a cationic charge, as shown above. The shift in the zeta potential of the spores caused by exposure to formulation D2 clearly indicates adsorption of the germicidal quaternary ammonium compound, i.e., the presence of the polymeric counterion does not interfere with the adsorption process. Since the magnitude of the shift of the zeta potential is somewhat smaller for exposure to formulation D2 compared to D1, it is believed, without being bound by theory, that the adsorption of some of the anionic polymeric counterion onto the spores also occurs, changing the overall chemistry of the adsorbed layer.

Surprisingly, exposure of the spores to formulation D3 also causes a significant shift of the zeta potential in the cationic direction, to a value only slightly below 0. Thus, even when the absolute value of P/Dnet is much greater than 1, indicating an excess of the anionic charges due to the polymeric counterion over that of the cationic charges due to the germicidal quaternary ammonium compound in the aggregates formed, significant adsorption of the germicide onto the spore surfaces still occurs. Thus, delivery of an adsorbed layer of germicidal quaternary ammonium compound onto the spores, which will be available to kill the bacteria upon germination, can be accomplished across a broad range of the absolute value of P/Dnet, which in turn allows adjustment of the formulations for other properties, such as oil solubilization, greasy soil removal during a cleaning process, and aesthetic properties such as lack of filming or streaking on solid surfaces.

Example 10

Antimicrobial Activity of Mixed Micelles Compared to Mixed Micelles with Polymeric Counterions (Micelle-Polymer Complexes) Against *Bacillus Subtilis* Spores A simple method was developed to demonstrate the utility of formulations comprising mixed micelles of a germicidal quaternary ammonium compound with a water-soluble anionic polymeric counterion (micelle-polymer complexes) in killing bacterial spores placed in an environment favorable for germination.

Serial dilution of concentrated cell suspensions followed by plating on a solid growth medium is a common way to determine the viable cells, or colony forming units (CFU), in a the suspension. The CFU multiplied by the relevant dilution factor relates back to the viable microbes in the original suspension. Those skilled in the art recognize that the automated spreading of a spore suspension in a spiral formation from near the center to the periphery of a circular plate containing solid microbial growth medium (agar medium described in detail here) simultaneously accomplishes dilution and a way to determine the CFU/ml of the microbial suspension through deposition over an ever lengthening area of the solid medium. Standard recognition software can visualize colonies on the solid medium and calculate the CFU/ml of the original suspension based on the distance and number of colonies relative to the center of the plate. Such an approach is implemented with commercially available equipment, such as the Autoplater Model AP5000 (Advanced Instruments) used in the following examples.

Spores which have been treated with the inventive compositions will be killed upon germination when they are deposited onto the growth medium due to a combination of the presence of some residual amount of the aqueous formulation and the quaternary ammonium molecules which are strongly adsorbed onto the surface of the spore. The spiral plating of the spore suspension accomplishes an exponentially increasing amount of dilution of the spores in a spiral pattern on the growth medium. Thus, the concentration of the aqueous formulation deposited with the spores is exponentially decreased by dilution with the growth medium. In addition, the chemistry of the aqueous environment surrounding the spores changes dramatically towards one rich in nutrients such as proteins. Thus, the quaternary ammonium molecules and any other surfactants adsorbed on the surface of the spore will re-equilibrate with the surrounding growth medium through desorption (partial or complete) from the spore surface, and/or a displacement from the spore surface through the adsorption of other materials present in the growth medium. In other words, the spiral plating method exposes the spores suspended in the inventive compositions to an exponentially increasing "organic load", which is well-known in the art to interfere with and or prevent the antimicrobial action of common germicides such as quaternary ammonium compounds or biguanides.

When suspensions of spores in the inventive compositions are deposited on growth medium via the spiral plating technique, the spores nearest the center of the spiral pattern will be more likely to be killed upon germination by the adsorbed germicidal quaternary ammonium compound or biguanide, and thus there will be no colonies observed after incubation in this region. Thus, instead of the expected spiral pattern in which there are large numbers of colonies crowded together nearest the center of the plate, there will be a circular "hole" in the pattern due to the killing of the spores upon germination. Farther away from the central starting point of the spiral, where the huge dilution has decreased the ability of the adsorbed biocidal species to kill the spore upon germination as described above, viable colonies will appear and continue in a spiral to the outer edge of the plate. Thus, the diameter of the circular hole in the spiral pattern is larger for formulations which provide more killing of spores upon germination under favorable conditions.

The equipment used for the spiral plating of the suspensions of the treated spores yields a pattern in which the central hole has a diameter of about 2 cm when a high concentration of spores that are viable (in a control experiment, for example) are present at the start of the spiral pattern. If the treatment of the spores results in killing upon germination of all of the spores, then the maximum diameter of the hole is about 8 cm. Thus, values of the diameter of the central hole between about 2 cm and 8 cm, herein called the germicidal zone diameter, represent varying degrees of effectiveness of the treatment of the spores for prevention of the contamination of a surface by the germination of spores under extremely favorable conditions, with larger values of the diameter indicating better effectiveness. Such testing methods are thus a good indication of the efficacy of the inventive compositions under various real life use conditions where various organic loads may be present or applied.

The treatment formulations, and dilutions of them, were placed in the wells of a 96 well plate, 10 microliters of the standard spore suspension were added and allowed to age for 10 minutes, followed by the addition of 200 μl of sterile water, and then 20 μl of the spore suspensions were then spiral plated onto the plates containing growth media. The spore concentrations treated were all the same, about $1\times10^6$, which is similar to the number of spores treated with the compositions in the determination of the changes in the zeta potential of the spores described above. The plates were incubated overnight at 37° C., followed by a measurement of the diameter of the germicidal zone diameter.

Formulations comprising mixed micelles of the germicidal quaternary ammonium compound BTC® 1010 and an amine oxide were made as described above, over a range of P/Dnet values, using the anionic water-soluble polymer Alcosperse® 747 as the polymeric counterion. Formulations E1 through E5 contained the same quaternary ammonium compound concentration, while formulation E6 contained a significantly lower quaternary ammonium compound concentration. The relative amounts of quaternary ammonium compound and amine oxide in the mixed micelles, however, was the same. The compositions are shown in Table 10.1.

TABLE 10.1

Compositions for Testing Effects of Treatment of *Bacillus Subtilis* spores

| Formulation Name | Polymer Alcosperse ® 747 wt % | Amine Oxide, Ammonyx ® LO, wt % | Germicidal Quat, BTC ® 1010, wt % | Monoethanolamine wt % | P/D net |
|---|---|---|---|---|---|
| E1 | 0 | 1.8 | 0.2 | 0.1 | 0 |
| E2 | 0.00255 | 1.8 | 0.2 | 0.1 | −0.05 |
| E3 | 0.0255 | 1.8 | 0.2 | 0.1 | −0.5 |
| E4 | 0.051 | 1.8 | 0.2 | 0.1 | −1.0 |
| E5 | 0.102 | 1.8 | 0.2 | 0.1 | −2.0 |
| E6 | 0 | 0.225 | 0.025 | 0.1 | 0 |

To cover a large range of concentrations of the germicidal quaternary ammonium compound in the treatment of the spores, formulations E1 through E6 were used neat (dilution factor=1), and at various dilutions (dilution factors 0.5 to 0.03125, or 2× to 32× times dilution of the original formulation). The results obtained with the spiral plating test are summarized in Table 10.2

TABLE 10.2

Spiral plate results
Effects of Formulations on Viability of *Bacillus Subtilis* spores

| Formulation Name | Dilution Factor Prior to Spore Exposure: 1 | 0.5 | 0.25 | 0.125 | 0.0625 | 0.03125 | Absolute value, P/Dnet |
|---|---|---|---|---|---|---|---|
| | Spiral Plate Germicidal Zone diameter, cm | | | | | | |
| E1 | 8 | 7.5 | 5.7 | 4.8 | 3.7 | 2 | 0 |
| E2 | 7.9 | 7.4 | 5.6 | 5 | 4 | 2 | 0.05 |
| E3 | 7 | 7 | 6.4 | 4.7 | 4 | 2 | 0.5 |
| E4 | 8 | 7 | 6 | 5 | 3.7 | 2 | 1.0 |
| E5 | 8 | 7.5 | 5.8 | 5 | 3.5 | 2 | 2.0 |
| E6 | 4.6 | 2.5 | 2 | 2 | 2 | 2 | 0 |

The results in Table 10.2 show that Formulations E2 through E5 (all of which contain the same quaternary ammonium compound concentration) all exhibit excellent performance in killing the spores upon germination, as does the control formulation E1, when used neat (dilution factor 1), yielding germicidal zone diameters of 7 to 8 cm. Dilution of formulations E1 through E5 by 32× (factor 0.03125) results in zone diameters of 2 cm, indicating no significant effect on the growth of the spores when they are placed on the growth media. Surprisingly, formulations in which the absolute value of P/Dnet are 1, (indicating an equal number of anionic charges due to the polymeric counterion and the cationic charges due to the germicidal quaternary ammonium compound) or even 2 (indicating an excess in the number of anionic charges due to the polymeric counterion over the cationic charges due to the germicidal quaternary ammonium compound) exhibit killing performance comparable to that of the control formulation across a range of dilutions in this test, confirming the robustness of the adsorption of the germicidal quaternary ammonium compound onto the spore surfaces, and in line with the effects of the formulations as measured by the changes in the zeta potential of the spores, as described above.

Control Formulation E6 included no polymeric counterion. Formulation E6, when diluted 2× (factor 0.5) contains 0.0125% quaternary ammonium compound, and shows only a small amount of germicidal activity, as shown by a germicidal zone diameter of 2.5 cm. Formulations E2 through E5, when diluted 16× (factor 0.0625), also contain 0.0125% quaternary ammonium compound. However, due to the presence of the polymeric counterion in these inventive compositions, the germicidal activity is significantly better than in the case of formulation E6. The germicidal zone diameters measured for treatment of spores with E2 through E5, at the dilution factor of 0.0625, are all significantly greater than that of formulation E6 at the dilution factor of 0.5, indicating the significant benefit of the presence of the anionic polymeric counterion in ensuring the kill of spores during germination under favorable conditions. Applicants speculate, without being bound by theory, that the presence of the anionic polymeric counterion along with the germicidal quaternary ammonium compound in the adsorbed layers formed on the spore surfaces decreases the tendency of the germicidal quaternary ammonium compound to desorb from the spore surface upon dilution of the spores in the growth medium and/or decreases the tendency of other surface-active molecules in the growth medium from competitively displacing the germicidal quaternary ammonium compound from the surface of the spores, thus providing improved germicidal performance of the inventive formulations compared to the control formulation containing mixed micelles without a polymeric counterion.

Example 11

Antimicrobial Activity of Mixed Micelles Compared to Mixed Micelles with Polymeric Counterions (Micelle-Polymer Complexes) Against *Bacillus Subtilis* Spores Some additional inventive formulations were developed covering a range of P/Dnet values and tested for activity against the growth of spores in the same manner as described in Example 10. A comparison with the activity of the control formulation E6 was also made, for the reasons described in Example 10.

TABLE 11.1

Compositions for Testing Effects of Treatment of *Bacillus Subtilis* spores

| Formulation Name | Polymer Alcosperse ® 747 wt % | Amine Oxide, Ammonyx ® LO, wt % | Germicidal Quat, BTC ® 1010, wt % | Monoethanolamine wt % | P/D net |
|---|---|---|---|---|---|
| F1 | 0.00255 | 0.2 | 1.8 | 0.1 | −0.05 |
| F2 | 0.0051 | 0.2 | 1.8 | 0.1 | −0.1 |
| F3 | 0.0102 | 0.2 | 1.8 | 0.1 | −0.2 |
| F4 | 0.0153 | 0.2 | 1.8 | 0.1 | −0.3 |
| F5 | 0.0204 | 0.2 | 1.8 | 0.1 | −0.4 |
| F6 | 0.0459 | 0.2 | 1.8 | 0.1 | −0.9 |
| E6 | 0 | 0.225 | 0.025 | 0.1 | 0 |

TABLE 11.2

Spiral plate results - Effects of Formulations on Viability of *Bacillus Subtilis* spores

| Formulation Name | Dilution Factor Prior to Spore Exposure | | | | | | Absolute value, |
|---|---|---|---|---|---|---|---|
| | 1 | 0.5 | 0.25 | 0.125 | 0.0625 | 0.03125 | P/Dnet |
| | Spiral Plate Germicidal Zone diameter, cm | | | | | | |
| F1 | 8 | 6.8 | 5.7 | 5.3 | 4 | 2.3 | 0.05 |
| F2 | 7.8 | 7.5 | 6.3 | 5.1 | 4 | 2.3 | 0.1 |
| F3 | 8 | 6.8 | 6.3 | 5 | 4.2 | 2.3 | 0.2 |
| F4 | 8 | 7.5 | 6 | 5.2 | 4.2 | 2.2 | 0.3 |
| F5 | 8 | 7.5 | 5.8 | 5 | 4 | 2.2 | 0.4 |
| F6 | 8 | 7.3 | 6.2 | 5.5 | 4 | 2.3 | 0.9 |
| E6 | 4.6 | 2.5 | 2 | 2 | 2 | 2 | 0 |

The results in Table 11.2 again indicate that formulations of the instant invention exhibit excellent germicidal performance, killing spores placed in an extremely favorable environment. In addition, the formulations show better performance at dilutions of 16× (factor 0.0625) than the control, which delivers the same total quaternary ammonium compound concentration of control formulation E6 at a 2× dilution (factor 0.5). The similarity in killing performance of the inventive compositions across a range of the absolute value of P/Dnet shows that optimization of other parameters of the formulations, such as cost, cleaning performance or kinetics, or surface residue aesthetics can be adjusted via P/Dnet while maintaining the antimicrobial properties of the formulations, due to the fine control of the interactions of the surfactants in the mixed micelles that can be achieved with the use of a water-soluble polymeric counterion of charge opposite to that of the net charge of the mixed micelles.

Example 12

Antimicrobial Mixed Micelles with Polymeric Counterions (Micelle-Polymer Complexes) Delivered from a Nonwoven Formulations comprising polymer micelle complexes comprised of mixed micelles of a germicidal quaternary ammonium compound and an amine oxide and anionic water soluble polymers increase the antimicrobial efficacy of a formula delivered by a nonwoven wipe. In this example polymer micelle complexes formulated over a range of P/Dnet values are shown to outperform mixed micelles in the ASTM International, Standard Practice for Evaluation of Pre-Saturated or Impregnated Towelettes for Hard Surface Disinfection, Test Method E 2362 (henceforth referred to as the towelette test) against *Pseudomonas*. This example also demonstrates flexibility in choice of polymer chemistry and the compatibility of micelle-polymer complexes with solvents and silver ions.

Compositions and P/Dnet values of the formulations are shown in Table 12.1. Formulations we prepared by first mixing BTC® 1010 (Stepan Co.) and Ammonyx® LO (Stepan Co.) in the specified amounts with water, thus forming the mixed micelles. The pH was then adjusted using MEA and glycolic acid in the specified amounts. The specified amount of anionic polymer (Alcosperse® 747. Alcoguard® H5240 or Alcoguard® 2300, all from Akzo Nobel) were then added to form the micelle-polymer complexes. Propylene glycol n-butyl ether (Dowanol™ PnB, Dow Chemical Co.) was added to formulation G3 to demonstrate compatibility with solvents. Silver dihydrogen citrate (Tinosan® SDC, Ciba) was added to formulation G6 at a raw material concentration of 0.125 wt % (equal to 3 ppm silver ions) to demonstrate compatibility with silver ions. The formulations form stable aggregates, characterized by DLS analysis as described in examples 1-6 and were visually clear.

Moist towelettes were prepared for ASTM Test Method E 2362 by applying the appropriate formulation to a roll of the towelettes. The mass of the liquid formulation added to the rolls of towelettes was 4.5 times the mass of the dry towelettes. Towelettes used in this example were nonwoven, 40 gsm material purchased from N.R. Spuntech Industries Ltd. The moist towelettes were allowed to equilibrate at room temperature for at least 24 hours.

TABLE 12.1

Compositions suitable for delivery from nonwovens

| Formulation Name | BTC ® 1010 wt % | Ammonyx ® LO wt % | Alcosperse ® 747 wt % | Alcoguard ® 2300 | Alcoguard ® 5240 | MEA wt % | Glycolic acid, wt % | PnB, wt % | Tinosan ® SDC, wt % | P/Dnet |
|---|---|---|---|---|---|---|---|---|---|---|
| G1 | 0.36 | 0.227 | 0 | 0 | 0 | 0.1 | 0 | 0 | 0 | 0 |
| G2 | 0.36 | 0.227 | 0.0099 | 0 | 0 | 0.1 | 0 | 0 | 0 | −0.05 |
| G3 | 0.36 | 0.227 | 0.0099 | 0 | 0 | 0.1 | 0 | 2 | 0 | −0.05 |

TABLE 12.1-continued

| Compositions suitable for delivery from nonwovens | | | | | | | | | | |
|---|---|---|---|---|---|---|---|---|---|---|
| Formulation Name | BTC ® 1010 wt % | Ammonyx ® LO wt % | Alcosperse ® 747 wt % | Alcoguard ® 2300 | Alcoguard ® 5240 | MEA wt % | Glycolic acid, wt % | PnB, wt % | Tinosan ® SDC, wt % | P/Dnet |
| G4 | 0.36 | 0.227 | 0 | 1.014 | 0 | 0 | 0.066 | 0 | 0 | −1.3 |
| G5 | 0.36 | 0.227 | 0 | 0 | 0.0042 | 0.05 | 0.1 | 0 | 0 | −0.025 |
| G6 | 0.5 | 0.32 | 0.002 | 0 | 0 | 1 | 0 | 0 | 0.125 | −0.007 |

TABLE 12.2

| Antimicrobial activity of formulations delivered from nonwovens. | |
|---|---|
| Formulation Name | Towelette 60 carrier test against *Pseudomonas* - 3 minute contact time |
| G1 | Fail |
| G2 | Pass |
| G3 | Pass |
| G4 | Pass |
| G5 | Pass |
| G6 | Pass |

Comparing formulations G1 and G2 show that addition of a small amount of anionic polymer to form micelle-polymer complexes characterized by P/Dnet=−0.05 increases the antimicrobial efficacy against *Pseudomonas* enough to generate a passing result. Formulation G3 shows that the microefficacy of formulation G2 is preserved when 2 wt % of PnB is added to the formulation, which may be desirable for robustness of the formula as well as a variety of aesthetic benefits. Formulations G4 and G5 demonstrate that a wide range of water soluble polymers are suitable for forming the micelle-polymer complexes. Formulation G4 also shows that micelle-polymer complexes formulated at an absolute value of P/Dnet greater than 1.0 are capable of boosting antimicrobial activity relative to that of mixed micelles without the polymeric counterions as well. This result is particularly surprising considering that the cationic charge on the germicidal micelles is widely accepted to be the driving force for adsorption of the active ingredients onto microbes. Finally, formulation G6 demonstrated the compatibility of the micelle-polymer complexes with silver ions.

Example 13

Kinetic Benefits of Antimicrobial Mixed Micelles with Polymeric Counterions (Micelle-Polymer Complexes) Delivered from a Nonwoven Two of the formulations described in Example 12 were tested at 1 minute contact times against *Staphylococcus Aureus* and *Pseudomonas* using the ASTM International, Standard Practice for Evaluation of Pre-Saturated or Impregnated Towelettes for Hard Surface Disinfection. Test Method F 2362. These formulas demonstrate passing antimicrobial efficacy at contact times considered to be extremely short for quaternary ammonium compound-based formulas. Formula G1, a mixed micelle control which delivers the same concentration of germicidal quat without the polymeric counterion, is not capable of passing the towelette test at 3 minute contact times (see example 12).

TABLE 13.1

| Antimicrobial activity of formulations delivered from nonwovens. | | |
|---|---|---|
| Formulation Name | Towelette 60 carrier test against *Staphylococcus Aureus* - 1 minute contact time | Towelette 60 carrier test against *Pseudomonas* - 1 minute contact time |
| G2 | Pass | Pass |
| G6 | Pass | Pass |

Example 14

Dilutable Formulations of Antimicrobial Mixed Micelles with Polymeric Counterions (Micelle-Polymer Complexes) on Laundry Dilutable formulations which may claim sanitization of laundry are governed by the document EPA DIS/TSS-13 "Laundry Additives—Disinfection and Sanitization". Such formulations must be demonstrated to reduce the levels of bacteria (both Gram + and Gram −) by at least 99.9% in a specific test protocol known as the "Petrocci and Clark Laundry Additives Method (sanitizing level)".

This example demonstrates the delivery of antimicrobial efficacy benefits using dilutable formulations comprising polymer-micelle complexes comprising mixed micelles of a germicidal quaternary ammonium compound and an amine oxide and anionic water soluble polymers. In this formulation BTC® 818 and Ammonyx® DO are mixed in water at the given concentrations, and then Alcoguard 5240 is added and mixed well. The formulation is visibly clear in the concentrated form and when diluted in hard water as per the laundry sanitizer test protocol.

TABLE 14.1

| Composition of formulations for a dilutable laundry sanitizer | | | | | |
|---|---|---|---|---|---|
| Formulation Name | Polymer Alcoguard ® 5240 wt % | Amine Oxide, Ammonyx ® DO, wt % | Germicidal Quat, BTC ® 818, wt % | P/D net | Laundry Sanitization Test - 1/584 dilution |
| H1 | 0.146 | 3.02 | 11.7 | −0.025 | Pass |
| H2 | 0 | 0 | 11.7 | 0 | Fail |

Formulation H1 is capable of passing the laundry sanitization test mentioned above against *Staphylococcus Aureus* and *Klesiella Pneumonia* at a 4 minute contact time when diluted 1 part to 584 parts in hard water. The extreme dilution ratio and high bacterial loads make this test method exceedingly difficult to pass with quaternary ammonium chemistries such as formulation H2.

Example 15

Oil Solubilization Enhancement with Polymer-Micelle Complexes Formed with an Anionic Polymeric Counterion and Mixed Micelles Consumers of aqueous based liquid cleaners frequently prefer fragranced formulations with excellent oily soil removal, while still demanding low residue on cleaned surfaces. The key to successfully satisfying this consumer demand is that the total concentration of solubilizer compounds be sufficiently high to fully incorporate the oily fragrance and any nonaqueous solvent compounds used to ensure excellent oily soil cleaning according to consumer preferences, while minimizing the total concentration to lessen the visual residue left on the cleaned surfaces, especially in the absence of a rinsing step. Applicants discovered that the interaction between mixed micelles comprising an amine oxide and germicidal quaternary ammonium compound and an anionic polymeric counterion according to one embodiment of the invention enables a unique and surprising oil solubilization boosting effect to satisfy these consumer preferences. In other words, similar results can be achieved with significantly less solubilizer when employing the inventive complexes.

The oil solubilization boosting effect of the polymer on the mixed micelles is readily illustrated by comparing the lowest total solubilizer concentration needed to solubilize 0.3 wt % limonene used as a model oily compound, such that the compositions are visibly clear, free of excess oil, precipitate and coacervate, in the absence and presence of the polymeric counterions. In this example, the total solubilizer concentration is the sum of the concentrations of the polymer, the germicidal quaternary ammonium compound BTC® 1010, and the nonionic surfactant Ammonyx® LO. The compositions are shown in Table 15.1.

TABLE 15.1

| Example | P/Dnet | BTC ® 1010 wt % | Ammonyx ® LO wt % | Alcosperse ® 465 | Limonene wt % | MEA wt % | Minimum total solubilizer need wt % |
|---|---|---|---|---|---|---|---|
| J1 | 0 | 0.05 | >1.2 | 0 | 0.3 | 0.1 | >1.25 |
| J2 | 0 | 0.1 | 1.275 | 0 | 0.3 | 0.1 | 1.375 |
| J3 | 0 | 0.15 | 1.35 | 0 | 0.3 | 0.1 | 1.5 |
| J4 | −0.01 | 0.05 | 0.596 | 0.96 | 0.3 | 0.1 | 0.646 |
| J5 | −0.01 | 0.1 | 0.754 | 1.93 | 0.3 | 0.1 | 0.854 |
| J6 | −0.01 | 0.15 | 0.981 | 2.89 | 0.3 | 0.1 | 1.131 |

In this example, the P/Dnet parameter was fixed at a relatively low absolute value, in order to minimize the cost of the polymer added to the formulation. Three different concentrations of BTC® 1010 were investigated. The lowest total solubilizer required in the absence of polymer was determined at various concentrations by making a series of formulations in which the concentration of the Ammonyx® LO was increased until the formulation was completely clear, corresponding to full solubilization of the limonene oil. Solubilization of the limonene was not achieved in the series of samples made that ended with the control formulation J1, which was a cloudy dispersion. Solubilization of the limonene could be achieved when the concentration of the BTC® 1010 cationic germicidal surfactant was increased somewhat, and if enough Ammonyx® LO was added, to give the final total solubilizer levels shown for formulations J2 and J3.

The same procedure was used to determine the minimum total solubilizer requirement in the presence of polymeric counterions at a fixed P/Dnet=−0.01 ratio. Appropriate amounts of the surfactant stock solution, monoethanolamine (to adjust pH above 9.0), limonene, and water were mixed to form the final control formulation containing the mixed micelles. In the case of formulations comprising the polymeric counterion, the same mixed surfactant stock solution, monoethanolamine, limonene, and Alcosperse® 465 (a poly (acrylic acid) homopolymer supplied as an aqueous solution. Akzo Nobel), and water were mixed in appropriate amounts to yield the final formulations with the fixed P/Dnet values, and increasing levels of Ammonyx® LO were added, thus varying the mixed micelle compositions, until a clear solution, indicating complete solubilization of the limonene, was obtained.

Comparing the optimized compositions in Table 15.1, it is apparent that the formulations with polymeric counterions (J4, J5 and J6) require lower total solubilizer concentrations, demonstrating a significant oil solubilization boosting effect resulting from the polymer-mixed micelle interaction. For example, formulation J5 requires only 0.854% total solubilizer to fully solubilize the limonene into a clear solution free of coacervates or precipitates, while formulation J2, which has the same concentration of the germicidal quaternary ammonium compound, requires a much higher total solubilizer level, 1.375%, to fully solubilize the same concentration of limonene.

Another unique aspect of the effect of the presence of the polymeric counterion is the remarkably low Alcosperse® 465 polymer concentration, in the ppm range, that is needed for the solubilization boosting. Thus, in formulations such as hard surface cleaners that may not be rinsed after use, very low levels of the polymeric counterion can dramatically also lower the total levels of surfactant needed to deliver a water-insoluble oil such as limonene, contributing to significant cost savings as well as a reduction or elimination of consumer-perceptible residues on surfaces cleaned with the formulations.

Example 16

Oil Solubilization Enhancement

The enhancement or boosting of the solubilization of water-insoluble oils may be obtained with a wide variety of water-soluble polymers, over a wide range of P/Dnet values, offering considerable flexibility in meeting different antimicrobial performance, aesthetic or cost targets.

Oil solubilization optimization is carried out in the presence of 0.3 wt % limonene model oil by, in a series of samples, simultaneously increasing the absolute value of P/Dnet and the concentration of the nonionic amine oxide surfactant at a fixed cationic surfactant concentration until solutions which are clear, free of precipitate, coacervate and excess oil are obtained. Optimized compositions are thus the ones that turn clear at the lowest added amine oxide surfactant concentration. The minimum total solubilizer values are thus the sum of the BTC® 1010, Ammonyx® LO, and polymer (if present) in the final formulations that yield complete oil solubilization.

Appropriate amounts of BTC® 1010, Ammonyx® LO, monoethanolamine (to adjust pH above 9.0), limonene, and water were mixed to form two series of samples in which the Ammonyx® LO level was increased at fixed BTC® 1010 concentrations until final control formulations K1 and K5, containing the mixed micelles and the solubilized limonene were obtained.

In the case of formulations comprising the polymeric counterion, the same surfactants, monoethanolamine, limonene, and Alcosperse® 747 (supplied as an aqueous solution, Akzo Nobel), and water were mixed in appropriate amounts to yield series of samples in which the mixed micelle compositions were changed by increasing amounts of Ammonyx® LO, at several different, fixed P/Dnet values. The optimized compositions, all of which are clear and free of coacervate, precipitate and excess oil, are summarized in Table 16.1.

TABLE 16.1

| Example | $P/D_{net}$ | BTC ® 1010 wt % | Ammonyx ® LO wt % | Alcosperse ® 747 ppm | Limonene wt % | MEA wt % | Minimum total solubilizer need wt % |
|---|---|---|---|---|---|---|---|
| K1 control | 0 | 0.1 | 1.275 | 0 | 0.3 | 0.1 | 1.426 |
| K2 | −0.1 | 0.1 | 1.09 | 510 | 0.3 | 0.1 | 1.241 |
| K3 | −1 | 0.1 | 0.91 | 510 | 0.3 | 0.1 | 1.061 |
| K4 | −2 | 0.1 | 0.91 | 510 | 0.3 | 0.1 | 1.061 |
| K5 control | 0 | 0.2 | 1.275 | 0 | 0.3 | 0.1 | 1.577 |
| K6 | −1 | 0.2 | 1.091 | 1020 | 0.3 | 0.1 | 1.393 |
| K7 | −2 | 0.2 | 0.545 | 1020 | 0.3 | 0.1 | 0.847 |

The results in Table 16.1 show that inventive formulations K2, K3, and K4 achieve complete limonene solubilization at lower total solubilizer levels than formulation K1, indicating an enhancement or "boosting" of the solubilization of the water-insoluble oil when the water-soluble anionic copolymer is used as the polymeric counterion for the mixed micelles bearing a net cationic charge. Surprisingly, the oil solubilization boosting can be achieved over a wide range of the absolute value of P/Dnet, i.e., oil solubilization enhancement can be achieved with a wide range of compositions of mixed micelles due to the fine control over the interactions between the cationic and nonionic surfactants in the mixed micelles that is possible through the use of the anionic polymeric counterion. Similarly, formulations K6 and K7 exhibit lower minimum total solubilizer concentrations than formulation K5.

Example 17

Antimicrobial Compositions Containing a Monomeric Biguanide, Chlorhexidine Gluconate The cationic germicide present in the mixed micelles may be a monomeric biguanide salt, such as chlorhexidine gluconate (CHG). CHG was supplied as 20% solution in water, from Sigma-Aldrich. CHG has two cationic charges per molecule and a molecular weight of 897.8 g/mole. The mixed micelles may also comprise nonionic surfactants. The compositions summarized in Table 17.1 comprise two nonionic surfactants, Surfonic® L12-8 (an alcohol ethoxylate, from Huntsman Corp), and Glucopon® 325N (an alkyl glucoside, from BASF Corporation) in the mixed micelles with the CHG. Since the CHG concentration is the same in formulations L1, L2 and L3, the value of Eq cationic will also be the same and is calculated as follows:

Eq cationic=2×0.015×1/897.8=3.34×$10^{-5}$ equivalents/100 g of formulation. And, since there is no anionic surfactant present in the formulation, then $$D\text{net}=D\text{ cationic}=+1\times 0.0000334=+3.34\times 10^{-5}$$

The water-soluble polymer used in this example as the polymeric counterion is poly(2-acrylamido-2-methyl-1-propanesulfonic acid), or polyAMPS. It has 1 anionic charge per monomer unit, which has a molecular weight of 207.25 g/mole. In formulation L1, polyAMPS is present at a concentration of 0.0035 wt % or 0.0035 gram/100 grams of the formulation.

P is thus calculated as $$P=0.0035\times 1\times 1\times(-1)/207.25=-0.0000168878.$$

$$\text{Thus, } P/D\text{net}=-0.0000168878/+3.34\times 10-5=-0.5053$$

The values of P and P/Dnet for the other formulations are summarized in Table 17.1

TABLE 17.1

| | composition, wt % | | |
|---|---|---|---|
| Ingredient | L1 | L2 | L3 |
| CHG | 0.015 | 0.015 | 0.015 |
| Surfonic ® L12-8 | 0.35 | 0.016 | 0.016 |
| Glucopon ® 325N | 0.8 | 0.037 | 0.037 |
| poly(2-acryl-amido-2-methyl-1-propanesulfonic acid) | 0.0035 | 0.014 | 0.035 |
| Dowanol ™ DB | 3.2 | | |
| Dowanol ™ PnB | 0.7 | | |
| Monoethanol-amine | 0.5 | | |
| NaCl | | 0.6 | 0.6 |
| Fragrance oil | 0.2 | | |
| pH | 11 | 7 | 7 |
| D net | $3.3415\times 10^{-5}$ | $3.3415\times 10^{-5}$ | $3.3415\times 10^{-5}$ |
| P | $-1.68878\times 10^{-5}$ | $-6.75513\times 10^{-5}$ | −0.0001689 |
| P/Dnet | −0.50539606 | −2.021584238 | −5.0539606 |

The negative values of P/Dnet for the formulations in Table 17.1 indicates that the polymer and mixed micelles are of opposite charge, and hence within the scope of the instant invention. The formulations also illustrate that fragrance oil may be solubilized in the mixed micelles, that the formulations may comprise water-soluble glycol ethers or not, and that the pH and electrolyte levels of the formulations may be varied with appropriate adjuvants such as monoethanolamine and sodium chloride. Formulation L1 is useful as a ready to use hard surface cleaner, while formulations L2 and L3 are useful as lotions for pre-moistened wipes or as hand sanitizers. Dowanol™ DB and Dowanol™ PnB are glycol ether solvents from Dow Corporation. Fragrance oil was a lemon fragrance from Firmenich.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

The invention claimed is:

1. A composition comprising:

a polymer-micelle complex comprising:

a positively charged micelle, wherein said positively charged micelle comprises a water-soluble cationic material selected from the group consisting of a monomeric quaternary ammonium compound, a monomeric biguanide, and mixtures thereof, said micelle is electrostatically bound to a polymeric counterion bearing a negative charge;

wherein said water-soluble polymer does not comprise a block copolymer, latex particles, polymer nanoparticles, cross-linked polymers, silicone copolymer, fluorosurfactant, or amphoteric copolymer;

wherein said composition does not form a coacervate, and wherein said composition does not form a film on a surface; and wherein said composition does not comprise a polyelectrolyte complex.

2. The composition of claim 1, wherein the polymeric counterion is a copolymer of acrylic acid and styrene.

3. The composition of claim 1, wherein the polymeric counterion is a copolymer of a polysaccharide and a synthetic monomer.

4. The composition of claim 1, wherein the polymeric counterion is a copolymer of maleic acid and sulfonated styrene.

5. The composition of claim 1, wherein the polymeric counterion is a copolymer of a dimethylacrylamide and acrylic acid.

6. The composition of claim 1, wherein the polymeric counterion is a copolymer of acrylic acid and maleic acid.

7. The composition of claim 1, wherein the polymeric counterion is a copolymer of sulfonated styrene and maleic anhydride.

8. The composition of claim 1, wherein the composition comprises a surfactant.

9. The composition of claim 1, wherein the composition comprises a buffer.

10. The composition of claim 1, wherein the composition comprises a fragrance.

11. The composition of claim 1, wherein the composition comprises a dye.

12. The composition of claim 1, wherein the composition comprises a colorant.

13. A composition comprising:

a polymer-micelle complex comprising:

a positively charged micelle, wherein said positively charged micelle comprising a water-soluble cationic material is selected from the group consisting of a monomeric quaternary ammonium compound, a monomeric biguanide, and mixtures thereof, said micelle is electrostatically bound to a polymeric counterion bearing a negative charge;

wherein the polymeric counterion is selected from a copolymer of a polysaccharide and a synthetic monomer; and wherein said water-soluble polymer does not comprise a block copolymer, latex particles, polymer nanoparticles, cross-linked polymers, silicone copolymer, fluorosurfactant, or amphoteric copolymer;

and wherein said composition does not comprise a polyelectrolyte complex.

* * * * *